US012642872B2

(12) United States Patent
Hetz Flores et al.

(10) Patent No.: US 12,642,872 B2
(45) Date of Patent: Jun. 2, 2026

(54) VIRUS AAV/IGF2, GENETIC TREATMENT METHOD AND USE THEREOF IN PROTEIN MISFOLDING-RELATED DISEASES, SUCH AS HUNTINGTON'S DISEASE

(71) Applicant: UNIVERSIDAD DE CHILE, Santiago (CL)

(72) Inventors: Claudio Andrés Hetz Flores, Independencia (CL); Paula García Huerta, Independencia (CL)

(73) Assignee: UNIVERSIDAD DE CHILE, Santiago (CL)

( * ) Notice: Subject to any disclaimer, the term of this patent is extended or adjusted under 35 U.S.C. 154(b) by 422 days.

(21) Appl. No.: 16/472,794

(22) PCT Filed: Dec. 21, 2017

(86) PCT No.: PCT/CL2017/000040
§ 371 (c)(1),
(2) Date: Jun. 21, 2019

(87) PCT Pub. No.: WO2018/112672
PCT Pub. Date: Jun. 28, 2018

(65) Prior Publication Data
US 2020/0030391 A1 Jan. 30, 2020

(30) Foreign Application Priority Data
Dec. 21, 2016 (CL) .................................. 3282-2016

(51) Int. Cl.
| *A61K 48/00* | (2006.01) |
| *A61P 25/28* | (2006.01) |
| *C07K 14/65* | (2006.01) |
| *C12N 15/85* | (2006.01) |
| *C12N 15/864* | (2006.01) |

(52) U.S. Cl.
CPC ............ *A61K 48/005* (2013.01); *A61K 48/00* (2013.01); *A61K 48/0075* (2013.01); *A61P 25/28* (2018.01); *C07K 14/65* (2013.01); *C12N 15/85* (2013.01); *C12N 15/8645* (2013.01); *A61K 48/0058* (2013.01); *C12N 2750/14143* (2013.01)

(58) Field of Classification Search
CPC .. A61K 48/005; A61K 48/0075; A61K 48/00; C07K 14/65; C12N 15/8645; C12N 2750/14143
USPC ...................... 514/44 R; 435/320.1; 424/93.6
See application file for complete search history.

(56) References Cited

U.S. PATENT DOCUMENTS

2012/0266263 A1 10/2012 Alberini et al.
2016/0243260 A1 8/2016 Blits

FOREIGN PATENT DOCUMENTS

| ES | 2442242 A1 | | 2/2014 |
| WO | WO 97/21449 | * | 6/1997 |
| WO | 2009034127 A1 | | 3/2009 |
| WO | 2014/085621 A1 | | 6/2014 |

OTHER PUBLICATIONS

Pascaul-Lucas et al. (2014) EMBO Mol. Med., vol. 6(10), 1246-1262.*
Allodi et al. (May 16, 2016) Scientific Reports, vol. 6:25960/doi:10.1038/srep25960, p. 1-14.*
Choi et al. (2014) Molecular Brain, vol. 7:17,http://www.molecularbrain.com/content/7/1/17, pp. 1-10.*
Salegio et al. (2010) Human Gene Therapy, vol. 21, 1093-1103.*
Zweig et al. (1992) vol. 49, 152-156.*
Ojala et al. (2015) The Neuroscientist, vol. 21 (1), 84-98.*
Glorioso et al. (2015) Gene Therapy, vol. 22, 931-933.*
Shahmoradi et al. (2015) PNAS: doi/10.1073/pnas.1423989112, pp. E3582-E3589.*
International Search Report and Written Opinion for related International Application No. PCT/CL2017/000040, mailed on Apr. 9, 2018; English translation of ISR provided; 18 pages.
Pascual-Lucas, M. et al. "Insulin-like growth factor 2 reverses memory and synaptic deficits in APP transgenic mice" EMBO Molecular Medicine, 2014; pp. 1246-1262; vol. 16, No. 10; 17 pages.
Allodi, I. et al. "Differential neuronal vulnerability identifies IGF-2 as a protective factor in ALS" Scientific Reports. May 16, 2016; 14 pages; vol. 6.
Shahmoradi, A. et al. "Enhanced memory consolidation in mice lacking the circadian modulators Sharp1 and -2 caused by elevated Igf2 signaling in the cortex" Proceedings of the National Academy of Science, Jun. 22, 2015; pp. E3582-E3589; 112(27); Cited as Ref. 3 in ISR.
Grieger, J. C. et al. "Production and characterization of adeno-associated viral vectors" Nature Protocols, Nov. 9, 2006; pp. 1412-1428 (17 pages).
Balch, W.E., et al., Adapting Proteostasis for Disease Intervention, Feb. 15, 2008, Science, 319, pp. 916-919.
Leitman, J., et al., ER Stress-Induced elF2-alpha Phosphorylation Underlies Sensitivity of Striatal Neurons to Pathogenic Huntingtin, Mar. 3, 2014, PLoS One, e0090803, 10 pgs.
Lee, H., et al., IRE1 Plays an Essential Role in ER Stress-Mediated Aggregation of Mutant Huntingtin via the Inhibition of Autophagy Flux, Human Molecular Genetics, Jan. 1, 2012, 21(1), pp. 101-114.
Naranjo, J.R., et al., Activating Transcription Factor 6 Derepression Mediates Neuroprotection in Huntington Disease, J Clin Invest, Feb. 1, 2016, 126(2), pp. 627-638.
Vidal, R.L., et al., Targeting the UPR Transcription Factor XBP1 Protects Against Huntington's Disease Through the Regulation of FoxO1 and Autophagy, Hum Mol Genet, May 15, 2012, 21(10), pp. 2245-2262.
Vidal, R., et al., Converging Pathways in the Occurrence of Endoplasmic Reticulum (ER) Stress in Huntington's Disease, Corr Mol Med, Feb. 2011, 11(1), pp. 1-12.

(Continued)

*Primary Examiner* — Anne Marie S Wehbe
(74) *Attorney, Agent, or Firm* — Procopio, Cory, Hargreaves & Savitch LLP

(57) ABSTRACT

The invention relates to the expression of two molecules in viral vectors AAV/IGF2-HA and AAV/IGF2, the associated method and use thereof in the amelioration of protein misfolding-related diseases, such as Huntington's disease, as presented in the in vivo models in FIGS. 11/19.

9 Claims, 12 Drawing Sheets

Specification includes a Sequence Listing.

(56) References Cited

OTHER PUBLICATIONS

Smith, H.L., et al., The Unfolded Protein Response: Mechanisms and Therapy of Neurodegeneration, Brain, Aug. 2016, 139(Pt 8), doi: 10.1093/brain/aww101, pp. 2113-2121.

Scheper, W., et al., The Unfolded Protein Response in Neurodegenerative Diseases: A Neuropathological Perspective, Acta Neuropthol, Sep. 2015, 130(3), pp. 315-331.

Walter, P., et al., The Unfolded Protein Response: From Stress Pathway to Homeostatic Regulation, Science 334, Nov. 25, 2011, 334(6059), pp. 1081-1086.

Hetz, C., et al., XBP-1 Deficiency in the Nervous System Protects Against Amyotrophic Lateral Sclerosis by Increasing Autophagy, Genes Dev, Oct. 1, 2009, 23(19), pp. 2294-2306.

Valdes, P., et al., Control of Dopaminergic Neuron Survival by the Unfolded Protein Response Transcription Factor XBP1, PNAS, May 6, 2014, pp. 6804-6809, vol. 111, No. 18 (6 pages).

Kaspar, B.K., et al., Retrograde Viral Delivery of IGF-1 Prolongs Survival in a Mouse ALS Model, Science, Aug. 8, 2003, 301(5634), pp. 839-842.

Coutelle, O., et al., Embelin Inhibits Endothelial Mitochondrial Respiration and Impairs Neoangiogenesis During Tumor Growth and Wound Healing, EMBO Mol Med, May 2014, 6(5), pp. 624-639.

Mellott, T.J., et al., IGF2 Ameliorates Amyloidosis, Increases Cholinergic Marker Expression and Raises BMP9 and Neurotrophin Levels in Hippocampus of the APPswePS1dE9 Alzheimer's Disease Model Mice, PLoS One, 2014, 9(4): e94287, 12 pgs.

Heywood, W.E., et al., Identification of Novel CSF Biomarkers for Neurodegeneration and their Validation by a High-Throughput Multiplexed Targeted Proteomic Assay, Mol Neurodegener, 2015, 10:64, 16 pgs.

Ulusoy, A., et al., Dose Optimization for Long-Term rAAV-Mediated RNA Interference in the Nigrostriatal Projection Neurons, Molecular Therapy, Sep. 2009, vol. 17 No. 9, pp. 1574-1584 (11 pages).

Aberg, et al. "Increased Cerebrospinal Fluid Level of Insulin-like Growth Factor-II in Male Patients with Alzheimer's Disease," Journal of Alzheimer's Disease 48, 2015, pp. 637-646, DOI 10.3233/JAD-150351, IOS Press, 10 pages.

Graff, et al. "Nasal Drug Administration: Potential for Targeted Central Nervous System Delivery," Journal of Pharmaceutical Sciences, vol. 94, No. 6, Jun. 2005, pp. 1187-1195, 9 pages.

Carro, et al. "Therapeutic actions of insulin-like growth factor I on APP/PS2 mice with severe brain amyloidosis," Neurobiology of Aging, 27, 2006, pp. 1250-1257, 8 pages.

Christoff, Jeffrey J., "Gene Therapy: Therapeutic Mechanisms and Strategies," American Journal of Pharmaceutical Education, Spring 2001, vol. 65, p. 103, 1 page.

Costantini, et al. "Gene therapy in the CNS," Millennium Review, Gene Therapy, 7, 2000, 0969-7128/00, pp. 93-109, 17 pages.

Fernandez, et al. "The many faces of insulin-like peptide signalling in the brain," Nature Review, Neuroscience, vol. 13, Apr. 2012, pp. 225-239, 15 pages.

Franz, et al. "Intraspinal cord delivery of IGF-I mediated by adeno-associated virus 2 is neuroprotective in a rat model of familial ALS," Neurobiology of Disease, 33, 2009, pp. 473-481, 9 pages.

Gao, et al. "Clades of Adeno-Associated Viruses Are Widely Disseminated in Human Tissues," Journal of Virology, vol. 78, No. 12, Jun. 2004, pp. 6381-6388, 8 pages.

Garcia-Huerta, et al. "The intersection between growth factors, autophagy and ER stress: A new target to treat neurodegenerative diseases?," Brain Research, 1649, 2016, pp. 173-180, 8 pages.

Hetz, et al. "Disturbance of endoplasmic reticulum proteostasis in neurodegenerative diseases," Nature Reviews, Neuroscience, vol. 15, Apr. 2014, pp. 233-249, 17 pages.

Product Data Sheet, "pAAV-MCS Expression Vector," VPK-410, Cell Biolabs, Inc., 2010-2016, 10 pages.

Rivera, et al. "Insulin and insulin-like growth factor expression and function deteriorate with progression of Alzheimer's disease: Link to brain reductions in acetylcholine," Journal of Alzheimer's Disease, 8, 2005, IOS Press, pp. 247-268, 22 pages.

Zuleta, et al. "AAV-mediated delivery of the transcription factor XBP1s into the striatum reduces mutant Huntingtin aggregation in a mouse model of Huntingon's disease," Biochemical and Biophysical Research Communications, 420, 2012, pp. 558-563, 6 pages.

Fauli, Trillo C., "Tratado de Farmacia Galenica," Chapters 8, 9, 10, 13, Ed Luzan 5, SA, Madrid, Spain, 1993, 30 pages.

Gennaro A., Ed., "Remington: The Science and Practice de Farmacia," 20a ed., Lippincott Williams Wilkins, Philadelphia, Pennsylvania, US, 2003, Chapter 55, pp. 1015-1029, 15 pages.

Beal, M. Flint et al. Neurochemical and Histologic Characterization of Striatal Excitotoxic Lesions Produced by the Mitochondrial Toxin 3-Nitropropionic Acid. The Journal of Neuroscience, Oct. 1993, 13(10). pp. 4181-4192.

Beglinger, PhD, Leigh J. et al. Randomized Controlled Trial of Atomoxetine for Cognitive Dysfunction in Early Huntington Disease. NIH Public Access Author Manuscript. J Clin Psychopharmacol. Oct. 2009 ; 29(5): 484-487. doi:10.1097/JCP.0b013e3181b2ac0a. 7 pages.

Bordelon, Yvette M. et al. Energetic Dysfunction in Quinolinic Acid-Lesioned Rat Striatum. Journal of Neurochemistry. Lippincott—Raven Publishers, Philadelphia © 1997 International Society for Neurochemistry. J. Neurochem. 69, pp. 1629-1639 (1997).

Holland, Negin et al. The role of noradrenaline in cognition and cognitive disorders. Brain Review Article. Brain 2021: 144; pp. 2243-2256.

Ludolph, A.C. et al. 3-Nitropropionic Acid—Exogenous Animal Neurotoxin and Possible Human Striatal Toxin. The Canadian Journal of Neurological Sciences. Can. J. Neurol. Sci. 1991; 18: pp. 492-498.

McLin, Jessica Pilar et al. Differential susceptibility to striatal neurodegeneration induced by quinolinic acid and kainate in inbred, outbred and hybrid mouse strains. © The Authors (2006). Journal Compilation © Federation of European Neuroscience Societies and Blackwell Publishing Ltd. doi:10.1111/j.1460-9568.2006.05198.x. European Journal of Neuroscience, vol. 24, pp. 3134-3140, 2006.

Sheline, Christian T. et al. Mitochondrial Inhibitor Models of Huntington's Disease and Parkinson's Disease Induce Zinc Accumulation and Are Attenuated by Inhibition of Zinc Neurotoxicity in vitro or in vivo. Neuro-degenerative Diseases. Modeling Neurodegenerative Diseases in vivo. Neurodegener Dis 2013;11:49-58. DOI: 10.1159/000336558. Published online: May 24, 2012. © 2012 S. Karger AG, Basel 1660-2854/13/0111-0049 $38.00/0. Accessible online at: www.karger.com/ndd.

Troncoso-Escudero, Paulina et al. On the Right Track to Treat Movement Disorders: Promising Therapeutic Approaches for Parkinson's and Huntington's Disease. Frontiers in Aging Neuroscience. Published: Sep. 3, 2020. https://www.frontiersin.org/journals/aging-neuroscience#articles. Sep. 2020, vol. 12, Article 571185, pp. 1-28.

* cited by examiner

| Gen | Region | Regulation |
|:---:|:---:|:---:|
| Igf2 | St / Cx | Up (1, 6 - 1, 82) |
| Mmp14 | Cx | Up (1, 6) |
| Lrp4 | Cx | Up (1, 4) |
| Uhrf | St | Down (1, 85) |

VIRUS AAV/IGF2, GENETIC TREATMENT METHOD AND USE THEREOF IN PROTEIN MISFOLDING-RELATED DISEASES, SUCH AS HUNTINGTON'S DISEASE

CROSS-REFERENCE TO RELATED APPLICATIONS

This application is a U.S. National Stage entry of PCT Application No: PCT/CL2017/000040 filed Dec. 21, 2017, which claims priority to Chilean Patent Application No. 3282-2016, filed Dec. 21, 2016, the contents of which are incorporated herein by reference.

TECHNICAL FIELD OF THE PRESENT INVENTION

The present invention applies to the field of medicine, specifically in the process of protein folding, by the use of adeno-associated viruses (AAV) that overexpress the IGF2 growth factor in cells of the central nervous system (CNS), preferably in areas of motor and cognitive control, recovering and improving neuronal deterioration.

BACKGROUND AND DESCRIPTION OF THE STATE OF THE ART

Scientific research on CNS diseases has been of great interest in recent years, especially diseases related to degenerative neurological disorders. The treatment of diseases related to protein misfolding, such as Huntington's disease, has approaches with allopathic therapies (antipsychotics and antidepressants) to diminish the symptoms triggered by the death of neurons as a consequence of protein misfolding, but none to slow the degeneration or to reverse the damage that it has already caused.

With respect to Huntington's disease (HD), its genetic cause was discovered over 20 years ago, but the mechanisms that lead to neuronal dysfunction and cell death are just beginning to be determined.

During the determination of these mechanisms, it has been suggested that the general alteration of the proteostasis network is an important pathological event in the gestation of HD, where the emergence of stress of the endoplasmic reticulum (ER) stands out. In this organelle reside the proteins responsible for the activation of the unfolded protein response (UPR), a reaction signal that controls cell fate under ER stress.

HD is a neurodegenerative disorder characterized in a first stage by a cognitive deterioration and changes in personality, together with failure in motor control in a more advanced stage, which prevents the performance of daily life tasks, concluding with premature death of the patient. At the protein level, the disease is characterized by an expansion of more than 35 repetitions of glutamine within the huntingtin protein, giving it a dominant toxic function, which leads to the progressive accumulation of mutant huntingtin (mHtt) and the occurrence of neuronal loss in the striatum. Although the mechanisms of the effects generated by mHtt on neuronal function are still discussed, different publications suggest that global alterations to protein homeostasis (1) contribute to pathogenesis (2-5), including the alteration of protein degradation. associated with ER, vesicular traffic in ER and Golgi, axonal transport and disturbances in autophagy (6). All these events increase the protein load of the cells, disturbing their correct folding and maturation in the ER, generating chronic ER stress and neuronal dysfunction (7). The ER stress triggers the activation of the unfolded protein response (UPR), a signaling pathway that allows, in the first place, to mediate cellular adaptation to recover proteostasis.

However, chronic ER stress can induce cell death and neurodegeneration. It is important to note that ER stress has been linked to several neurodegenerative diseases, including amyotrophic lateral sclerosis (ALS), Alzheimer's disease (AD), and Parkinson's disease (PD) (7-9). Within this signaling, the most conserved branch is controlled by the X-box transcription factor of the binding protein 1 (XBP1) that controls the expression of a group of genes involved in different aspects of the proteostasis network (10). It was previously demonstrated that the deletion of XBP1 in neurons in mouse models with HD had a neuroprotective effect (5). In general, the animals were more resistant to developing the disease, associated with an improvement in neuronal survival and a better motor performance. This phenotype was explained by a drastic decrease in mHtt levels, possibly due to a positive regulation of autophagy (5). Similar observations were obtained in models of ALS (11) and PD (12).

In the search for a treatment of these protein-misfolding diseases, the insulin-like growth factor II, called IGF2, has been identified, whose function is involved in the biological and molecular mechanisms of fetal growth, as well as involved with some cancerous tumors.

IGF2 is a secreted growth factor with interesting neuroprotective activities in several models. In summary, some recent studies suggest that IGF, in general, are possible targets for the treatment of neurodegenerative diseases, particularly, considering their functions as neurogenic agents and neuroprotective effects (13). In fact, the delivery of IGF1 in preclinical models of AD and ALS attenuates the pathological characteristics by using gene therapy (14-16). In contrast to IGF1 and insulin, IGF2 has been little studied. Only a few recent reports suggest a neuroprotective role for IGF2, where it reduces amyloid plaques and cognitive impairment in AD models (17, 18). Similarly, in ALS, IGF2 is expressed differentially in motor neurons resistant to the disease and its overexpression by means of gene therapy delays the progression of the same (19). In addition, in humans, IGF2 levels decrease in the hippocampus of AD patients (17, 20), and also shows alterations in CSF samples (21, 22).

However, there are no functional studies having linked IGF2 with HD.

In general, the dynamics between the signaling of the UPR and that of the growth factors suppose a new approach linking the proteostasis network with the survival signals that modulate neuronal physiology (23). For these reasons, IGF2 represents an interesting candidate to study in the context of HD that can provide new therapeutic routes for its treatment, in addition to its potential use as a biomarker to monitor the progression of the disease.

In document CL 3510-2014, having international application WO2014/085621, where a fusion protein comprising IGF2 is presented for the treatment of diseases associated with lysosomal proteins, there is no mention of a genetic treatment to cure HD.

Also, there is a second document, ES 2442242 A1, which mentions a composition based on an extract drawn from blood which comprises different growth factors, where there was no mention either of genetic treatment to cure HD.

Therefore, there are no documents that use gene therapy linking the IGF2 gene and the treatment of HD.

SUMMARY OF THE INVENTION

In general, the invention aims to generate genetic therapeutic agents, therapies, identification devices and, uses to treat Huntington's disease. The specific technical objectives or problems to be solved are listed below:

A first aspect of the present invention relates to a method for improving or curing Huntington's disease, preferably in humans, by using a virus that allows IGF2 and/or IGF2-HA overexpression in the brain, preferably in the striatum and cortex.

A second aspect of the present invention provides a method of therapeutic treatment for improving or curing Huntington's disease. The method comprises intravenous and/or intraperitoneal and/or intracranial and/or intramedullary and/or intranasal and/or intraneural administration and/or any route that introduce the virus to the brain by crossing the blood-brain barrier of a patient or subject. The virus induces neuronal overexpression of IGF2 and/or IGF2-HA in a dose range of 16 to 130 viral units per individual.

A third aspect of the present invention is an intravenous and/or intraperitoneal and/or intracranial and/or intramedullary and/or intranasal and/or intraneural pharmaceutical composition and/or any form that deliver the virus inducing neuronal overexpression of IGF2 and/or IGF2-HA to the brain, preferably to the hippocampus, crossing the blood-brain barrier, with dose ranges as previously presented, and a pharmaceutically acceptable vehicle for use in the optimization and improvement of long-term memory of human patients with Huntington's disease.

A fourth aspect of the present invention is the use of a virus inducing neuronal overexpression of IGF2 and/or IGF2-HA and its protein derivative compounds as it serves to prepare a drug useful in the amelioration of Huntington's disease.

A fifth aspect of the present invention is a virus of the adeno-associated type (AAV) having the same virus sequence and an insert with a nucleotide sequence as described in Table II (SEQ ID No. 2) and Table III (SEQ ID No. 3) or any of its variants, contained in the *Escherichia coli* strain transformed with the plasmids deposited in the international depositary authority, Chilean Collection of Microbial Genetic Resources (CChRGM) having deposit numbers RGM2336 and RGM2335 where IGF2 and/or IGF2-HA growth factor is overexpressed, respectively, mainly in the striatum and cortex.

A sixth aspect of the present invention is the plasmid with the nucleic acid fragment of the virus and an insert with a nucleotide sequence as described in Tables II (SEQ ID No. 2) and III (SEQ ID No. 3) and contained in the *Escherichia coli* strain transformed with the plasmids deposited in the international depositary authority, Chilean Collection of Microbial Genetic Resources (CChRGM), having deposit numbers RGM2336 and RGM2335 and/or any variant of this fragment, encoding and overexpressing the IGF2 and/or IGF2-HA growth factor, respectively.

A seventh aspect of the present invention is to provide a method of diagnosing Huntington's disease.

An eighth aspect of the following invention is the use of a virus that induces overexpression of IGF2 and/or IGF2-HA and its protein derivative compounds as it serves to prepare a drug useful in the stabilization of physiological levels in patients with Huntington's disease.

The present patent also presents the sequence of the plasmid with the nucleic acid fragment of the virus and an insert with a nucleotide sequence as described in Tables IV (SEQ ID No. 4), V (SEQ ID No. 5), and VII (SEQ ID No. 6) or any variant of this fragment, which encode and overexpress IGF2 and/or IGF2-HA growth factor.

Deposit of Microorganisms

Plasmids pAAV-IGF2-HA and pAAV-IGF2 were deposited in 2016 at the international depositary authority, contained in the strain of *Escherichia coli* transformed with the plasmids deposited in the international depositary authority, Chilean Collection of Microbial Genetic Resources (CChRGM), having deposit numbers RGM2335 and RGM2336, respectively.

DETAILED DESCRIPTION OF THE INVENTION

It is to be understood that this invention is not limited to the particular methodology, compounds, materials, manufacture techniques, uses and applications described herein, as such may vary. It is also to be understood that the terminology used herein is for the purpose of describing a particular embodiment only, and it is not intended to limit the perspective and potential of the present invention.

It must be noted that as used herein, in the appended claims, and in the entire text, the singular forms include plural referents unless the context clearly dictates otherwise. Thus, for example, reference to "a use or method" includes reference to one or more uses or methods and include equivalents known to those skilled in the matter (the art). Similarly, as a further example, reference to "a step", "a stage", or "a mode" includes reference to one or more steps, stages, or modes, which may include implicit and/or supervening sub steps, stages, or modes.

Every conjunction used must be understood in its less restrictive and more inclusive possible meaning. For example, the conjunction "or" should be understood in its orthodox logic sense and not as an excluding "or", except when the context or text expressly requires it or states it. It is to be understood that the described structures, materials, and/or elements are also making reference to those functionally equivalent so that endless enumerations be avoided.

The expressions used to denote approximations or concepts should be understood in their intrinsically meaning, unless the context is expressing a different reading.

All technical and/or scientific names and terms used herein have the usual meaning given by a person of ordinary skill in this art, except when a different meaning is clearly expressed.

Methods, techniques, elements, compounds and compositions are described although similar and/or equivalent methods, techniques, elements, compounds and compositions to those already described can be used or preferred in practice and/or trials of the present invention.

All patents and other publications are included as a reference with the purpose of describing and/or informing, for example, the methodologies described in said publications that might be useful regarding the present invention.

The publications included herein are provided solely for their disclosure prior to the filing date of the present application.

In this regard, nothing should be interpreted as an admission or acceptance, rejection or exclusion that the authors and/or inventors are not entitled or that said publications are dated before other previous ones, or by any other reason, The present invention describes vectors based on the serotypes AAV1, AAV2, AAV3, AAV4 or any serotype, hybrids and also adeno-associated viruses capable of efficiently mediating the transfer of genes to the brain, preferably AAV2, preferably AAV2/2, preferably striatum and cortex (cortex), when administered locally. (FIGS. 10, 11 and 12).

Systemic administration of these vectors also leads to efficient gene delivery to both the brain and the striatum and cortex. Although the delivery of genes mediated by vectors AAV2 and AAV2/2 are more efficient, the delivery in the case of systemic administration is not restricted only to the brain or the striatum and cortex. The present invention shows that the vector AAV2 and AAV2/2 with the gene that encodes for the expression of the growth factor IGF2, allows the generation of a response in a cluster of factors of interest in the brain and, specifically, in the striatum and cortex.

Particularly, local administration of the AAV2/2 vector comprising an expression cassette in which an Igf2 gene is under the control of the CAG promoter obtains an improvement in the treatment of Huntington's disease in vivo. (FIGS. 11 and 12).

I. Definition of General Terms and Expressions

As used in the present document, the terms "adeno-associated virus", "AAV virus", "AAV virion", "AAV viral particle", and "AAV particle", are interchangeable and refer to a viral particle composed of at least one AAV capsid protein (preferably by all of the capsid proteins of a particular AAV serotype) and a polynucleotide of the encapsidated AAV genome. If the particle comprises a heterologous polynucleotide (i.e., a polynucleotide other than a wild-type AAV genome such as a transgene to be delivered to a mammalian cell) flanked by the AAV inverted terminal repeats, which is typically referred to as a "AAV vector particle" or "AAV vector". AAV refers to a virus belonging to the genus Dependovirus of the family Parvoviridae. The AAV genome is approximately 4.7 kilobases long and is composed of single-stranded deoxyribonucleic acid (ssDNA) that can be either positive-sense or negative-sense. The genome comprises inverted terminal repeats (ITR) at both ends of the DNA strand, and two open reading frames (ORFs): REP and CAP (Replicase and Capsid). The REP frame consists of four overlapping genes that encode for REP proteins (REP 78, REP 68, REP 52 and REP 40) required for the AAV life cycle. The CAP frame contains overlapping nucleotides of 20 capsid protein sequences: VP1, VP2, and VP3, which interact with each other to form a capsid having icosahedral symmetry (30), as presented in FIG. 15.

As used herein, the term "adeno-associated virus ITR" or "AAV ITR", refers to the inverted terminal that is repeated and present at both ends of the DNA strand of an adeno-associated virus genome. ITR sequences are required for efficient multiplication of the AAV genome. Another property of these sequences is their ability to form a fork. This characteristic contributes to its replication, which allows the primary synthesis separately from the second strand of DNA. ITRs also proved to be necessary both for the integration of the wild-type AAV DNA into the host cell genome and the rescue thereof, as well as for the efficient encapsidation of the AAV DNA combined with the generation of its complete assembly (25).

As used in the present invention, the terms "AAV2" and "AAV2/2" refer to serotype 2 of the adeno-associated virus, having a genome sequence as defined in accession number GenBank J01901.1, located on the website: https://www.ncbi.nlm.nih.gov/nuccore/J01901.1

From the eleven serotypes that have been characterized to date, the best characterized and most frequently used is AAV2. The difference between the different serotypes is determined by their cellular tropism, with AAV2 being one of the ones with the highest "affinity" for infecting cells of the central nervous system.

As used in the present invention, the term "AAV vector" further refers to a vector comprising one or more polynucleotides of interest (or transgenes) that are flanked by AAV terminal repeat (ITR) sequences. Said AAV vectors can be replicated and packaged into infectious viral particles when they are present in a host cell that has been transfected with a vector encoding and expressing the REP and CAP genes (i.e. the AAV proteins REP and CAP), and where the host cell has been transfected with a vector encoding and expressing a protein of the E4orf6 adenovirus reading frame. When an AAV vector is incorporated into a larger polynucleotide (for example, in a chromosome or in another vector such as a plasmid used for cloning or transfection), then the AAV vector is typically referred to as a "pro-vector". The pro-vector can be "rescued" by replication and encapsidation in the presence of the packaging functions of the AAV and the necessary auxiliary functions provided by E4orf6.

As used in the present invention, the term "CAP gene" or "AAV CAP gene" refers to a gene encoding a CAP protein. The term "CAP protein", as used herein, refers to a polypeptide having activity of at least one functional activity of the CAP protein of a wild-type AAV (VP1, VP2, VP3). Examples of functional activities of VP1, VP2, and VP3 proteins include the ability to induce the formation of a capsid, facilitating the accumulation of single-stranded DNA, facilitating the packaging of AAV DNA in the capsid (i.e., encapsidation), binding to cell receptors and facilitating the entry of the virion to a host.

As used in the present invention, the term "capsid", refers to the structure in which the viral genome is packaged. A capsid consists of an oligomeric structure with structural subunits of CAP proteins. For example, the AAV has an icosahedral capsid formed by the interaction of three capsid proteins: VP1, VP2 and VP3.

As used in the present document, the term "cell composition" refers to a composite type material comprising the cells of the invention and at least one other component. The composition can be formulated as a single formulation or be presented as separate formulations of each of the components, which can be combined for the joint use as a combined preparation. The composition can be a parts kit, where each of the components is formulated and packaged individually.

As used in the present invention, the term "constitutive promoter" refers to a promoter whose activity is maintained at a relatively constant level throughout an organism, or during most of the experimental steps, with little or no consideration to the environmental and external conditions of the cell.

As used herein, the term "expression cassette" refers to a construction of nucleic acids, generated by recombination or synthetically, having a series of specific elements of the nucleic acids, which allow the transcription of a particular nucleic acid in a target cell.

As used herein, the term "genes that provide helper functions" refers to genes encoding polypeptides performing functions on which the AAV is dependent for replication (i.e., "helper functions"). Auxiliary functions include those functions necessary for the AAV replication, including the fragments involved in the activation of AAV gene transcription, the specific splicing steps of AAV mRNA, the replication of AAV DNA, the synthesis of CAP products, and the assembly of the AAV capsid. Accessory viral functions can be derived from any of the known helper viruses such as adenovirus, herpes virus, lentivirus, and vaccinia virus. Auxiliary functions include, without limitation, WHV lentivirus.

As used herein, the term "locally administered" means that the polynucleotides, vectors, polypeptides, and/or pharmaceutical compositions of the invention are administered to the subject at or near a specific site.

In the present document, the terms "pharmaceutically acceptable carriers", "pharmaceutically acceptable diluents", "pharmaceutically acceptable excipient" or "pharmaceutically acceptable vehicle", are interchangeable and refer to a non-toxic, semi-solid, or liquid filler, diluent, or encapsulation material, or an auxiliary formulation for any conventional type. A pharmaceutically acceptable carrier is essentially non-toxic to the recipients used in the dosages and concentrations, and it is compatible with other ingredients of the formulation. The number and nature of pharmaceutically acceptable vehicles depend on the desired form of administration. Pharmaceutically acceptable carriers are known and can be prepared by methods well known in the art. (24)

As used herein, the term "promoter" refers to a nucleic acid that serves to control the transcription of one or more polynucleotides, located upstream from the polynucleotide(s) sequence, and which is structurally identified by the presence of a DNA-dependent RNA-polymerase binding site, transcription initiation sites, and any other DNA sequence, including, but not limited to, transcription factors binding sites, repressor, and activator protein binding sites, and any other nucleotide sequences known in the art that act directly or indirectly to regulate the amount of transcription from the promoter. A "tissue-specific" promoter is only activated in certain types of differentiated cells or tissues.

As used herein, the term "polynucleotide" refers to a nucleic acid molecule, either DNA or RNA, that contains deoxyribonucleotides or ribonucleotides, respectively. The nucleic acid may be double stranded, single stranded, or contain parts of either double stranded or single stranded sequences. The term "polynucleotide" includes, but is not limited to, nucleic acid sequences with the ability to encode a polypeptide and nucleic acid sequences partially or wholly complementary to an endogenous polynucleotide of the cell or the subject treated therewith so that, after transcription thereof, it generates an RNA molecule (for example, microRNA, shRNA, siRNA) capable of hybridizing and inhibiting the expression of the endogenous polynucleotide.

In this document, the term "strand" refers to a sequence of continuous nucleotides (including or not including modified natural nucleotides or unnatural nucleotides). The two or more strands can be, or each can form part of, separate molecules, or they can be covalently interconnected, for example, by means of a coupling, for example, a linker such as polyethylene glycol, to form a molecule. At least one of the chains can include a region that is sufficiently complementary to a target RNA.

As used herein, the term "recombinant viral genome", refers to an AAV genome in which at least one polynucleotide cassette foreign to the expression in the wild-type AAV genome is inserted.

As used herein, the term "rep gene" or "AAV rep gene", refers to a gene encoding a Rep protein. The term "Rep protein," as used herein, refers to a polypeptide having at least one functional activity of an AAV native rep protein (e.g., Rep 40, 52, 68, 78). A "functional activity" of a Rep protein (e.g. Rep 40, 52, 68, 78) is any activity associated with the physiological function of the protein, including the facilitation of DNA replication through recognition, binding, and cleavage of the AAV DNA replication origin, as well as the DNA helicase activity. Additional functions include modulation of AAV (or other heterologous) transcription promoters, and the site-specific integration of AAV DNA into a host chromosome.

As used herein, the term "subject" refers to an individual, plant, mammal or animal, such as a human, a non-human primate (e.g., chimpanzee or other ape and species of monkeys), an animal (e.g., birds, fish, cattle, sheep, pigs, goats, and horses), a mammal (e.g., dogs and cats), or a laboratory animal (e.g., rodents, such as mice, rats, mice with silenced genes (knockout mice), mice that overexpress a gene (transgenic mice) and guinea pigs). The term does not denote a particular age or sex. The term "subject" includes an embryo and a fetus.

As used herein, the term "systemically administered" and "systemic administration" means that the polynucleotides, vectors, polypeptides, or pharmaceutical compositions of the present invention are administered to a subject in an unlocalized form. The systemic administration of the polynucleotides, vectors, polypeptides, or pharmaceutical compositions of the invention can reach various organs or tissues throughout the body of the subject or reach new specific tissues or organs of the subject. For example, intravenous administration of a pharmaceutical composition of the invention can result in transduction in more than one tissue or organ in a subject. For the present invention, it also means that the polynucleotides, vectors, polypeptides, or pharmaceutical compositions of the invention that act systemically, operate close to or with neuronal nerve cells or with non-neuronal nerve cells, as well as intra- or extracellularly.

As used herein, the term "transduction" refers to the process by which a sequence of foreign nucleotides is introduced into the cell by a virus.

As used herein, the term "transfection" refers to the introduction of DNA into the recipient eukaryotic cells.

As used herein, the term "vector" refers to a construct capable of delivering, and optionally expressing, one or more polynucleotides of interest in a host cell. Examples of vectors include, but are not limited to, viral vectors, DNA or naked RNA expression vectors, plasmid, cosmid or phage vectors, RNA or DNA expression vectors associated with cationic condensation agents, DNA or RNA expression vectors encapsulated in liposomes, and certain eukaryotic cells, such as producer cells. Vectors can be stable and can be self-replicating. There are no limitations as to the type of vector that can be used. The vector can be a cloning vector, suitable for propagation and for obtaining polynucleotides, gene constructs, or expression vectors incorporated into various heterologous organisms. Suitable vectors include prokaryotic expression vectors, phage and shuttle vectors, and eukaryotic expression vectors based on viral vectors (e.g., adenoviruses, adeno-associated viruses, as well as retroviruses and lentiviruses), as well as non-viral vectors.

As used herein, the term "DARPP" is a dopamine-regulated phosphoprotein that is used as a marker of medium spiny neurons (MSNs), which are the major neurons affected by the expression of mHtt. Its expression is used as a viability marker.

The term IGF2, used in the document, refers to the IGF2 polypeptide per se, but also to the variants bound to the HA epitope.

The methods and compositions of the invention, for example the methods and compositions of the AAV with the insert IGF2-HA or simply IGF2, can be used with any dosage and/or formulation described in the present invention, as well as with any route of administration described in the present invention.

For the term "amelioration of Huntington's disease", we refer to the improvement of psychiatric, behavioral, and motor symptoms, as well as a decrease in huntingtin aggregates in different species and/or subjects as defined in the present invention.

The term "cDNA" or "complementary DNA" refers to a DNA sequence totally complementary to an RNA, from which it is synthesized by RT-PCR.

As used in this document, the term "complementary" is used to indicate such a sufficient degree of complementarity that a stable and specific binding occurs between a compound and a target RNA molecule, the specific binding requires a sufficient degree of complementarity to avoid non-specific binding of the oligomeric compound to non-target sequences under conditions where the specific binding is desired, i.e. under physiological conditions in the case of in vivo assays or therapeutic treatment, or in the case of in vitro assays under conditions in which the assays have been carried out.

Ligands

The properties of a virus, including its pharmacological properties, can be influenced and tailored, for example, by the introduction of ligands. In addition, the pharmacological properties of a viral agent can be enhanced by the incorporation of a ligand in a formulation of the agent and a virus.

Ligands can bind to a wide variety of entities, for example, ligands that bind to a viral agent, or that can be used as a conjugate or formulation additive, for example, with the vehicle of a ligand-conjugated monomer subunit. The examples are described below in the context of a ligand-conjugated monomer subunit, but that is only preferred, and entities can be coupled at other points with a virus.

A ligand alters the distribution, direction, or lifetime of a viral agent in which it is incorporated. In the preferred embodiments, a ligand provides a better affinity for a selected target, for example, a molecule, cell, or cell type, a compartment, for example, a cell or organ compartment, a tissue, or region of the body, for example, as compared to a species in which this ligand is absent.

Ligands can improve the transport, hybridization, and specificity properties of the target molecule, for the present invention, of the virus.

Ligands, in general, can include therapeutic modifiers, for example, to improve the absorption of the molecule in the individual; diagnostic compounds or reporter groups, for example, to monitor distribution; crosslinking agents; moieties that confer resistance to immune reactions; and natural or unusual nucleobases.

General examples include lipophilic molecules, lipids, lectins, (e.g., hecigenin, diosgenin), terpenes (e.g., triterpenes, e.g., sarsasapogenin, friedelin, epifriedelanol derivatized lithocholic acid), vitamins, carbohydrates (e.g., a dextran, pullulan, chitin, chitosan, synthetic polymers [e.g., oligo-lactate 15-mer] and natural polymers [e.g., with low and medium molecular weight], inulin, cyclodextrin, or hyaluronic acid), proteins, protein binding agents, integrin targeting molecules, polycations, peptides, polyamines, and peptide mimetics. Other examples include epithelial cell or folic acid receptor ligands, such as transferrin.

The ligand can be a molecule presented in a natural, recombinant, synthetic form, such as a synthetic polymer, for example, a synthetic polyamino acid. Examples of polyamino acids include poly-L-lysine (PLL), poly-L-aspartic acid, poly-L-glutamic acid, styrene-maleic anhydride copolymer, poly(lactic-co-glycolic acid) copolymer, divinyl ether-maleic anhydride, N-(2-hydroxypropyl)methacrylamide (HMPA) copolymer, polyethylene glycol (PEG), polyvinyl alcohol (PVA), polyurethane, poly(2-ethylacrylic acid), N-isopropylacrylamide polymers, or polyphosphazine. Examples of the polyamines include: polyethyleneimine, poly-L-lysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha-helical peptide.

Ligands can also include targeting groups, for example, a targeting agent to a cell or tissue, for example, a thyrotropin, melanotropin, surfactant protein A, mucin carbohydrate, a glycosylated polyamino acid, bisphosphonate, polyglutamate, polyaspartate, or a Arg-Gly-Asp (RGD) peptide, or a RGD peptide mimic.

Ligands can be proteins, for example, glycoproteins; lipoproteins, for example, low-density lipoprotein (LDL); or albumins, for example, serum albumin; or peptides, for example, molecules having a specific affinity for a co-ligand; or antibodies, for example, an antibody that binds to a specified cell type. Ligands can also include hormones and hormone receptors. They can also include non-peptidic species, such as cofactors, multivalent lactose, multivalent galactose, N-acetylgalactosamine, N-acetylglucosamine, multivalent mannose, or multivalent fucose.

The ligand can be a substance, for example, a drug, that can increase the absorption of the viral agent within the cell, for example, by altering the cytoskeleton of the cell, for example, by altering microtubules, microfilaments, and/or filaments intermediates of the cell.

In one aspect, the ligand is a lipid, or a lipid-based molecule. This lipid or this lipid-based molecule is preferably linked to a whey protein, for example serum albumin.

In an alternative embodiment, to those previously named, the viruses will be packed.

The injectable solutions of virus are prepared by diluting the necessary concentration of virus in PBS (phosphate-buffered saline) whose formulation is as follows:

PBS 1×

1. Dissolve the viral dose in 800 ml of distilled water with:
   8 g of NaCl
   0.2 g of KCl
   1.44 g of Na2HPO4
   0.24 g of KH2PO4
2. Adjust the pH to 7.4 with HCl.
3. Adjust the volume to 1 L with additional distilled water H2O.
4. Sterilize and autoclave.

Design and Selection

Controlling the expression of the mutant version of huntingtin is key to ameliorate or cure Huntington's disease.

In the cell, there are several mechanisms capable of degrading misfolded proteins, including the degradation associated with ER and autophagy. However, it is very difficult to selectively degrade a particular protein. Nevertheless, studies carried out to date indicate that IGF2 is able to reduce, in some way, the expression of huntingtin, thus reducing its toxic function.

In addition to requiring the modulation of local protein synthesis, the amelioration or cure for Huntington's disease involves other aspects in the secretory pathway including the synthesis and trafficking of various membrane receptors and ion channels, the increase in calcium signaling, the synthesis of membranes, and the assembly of protein complexes. However, a unique function of IGF2 was found preferentially, but not exclusively, in the striatum and cortex.

The application example, described herein, provides proof that IGF2 decreases the expression of mHtt and increases neuronal viability, slowing down the development of Huntington's disease.

When analyzing the biomedical scope of its use as therapy, an effective and innovative method was provided to ameliorate or treat Huntington's disease, in which the use of this technology produces surprising results in its application.

Experimentally, it has been reported that overexpression of IGF2 in the context of HD, drastically decreases the aggregates of polyglutamine peptides, as well as mutant huntingtin. In addition, a neuroprotective effect was observed, with an increase in the survival of medium spiny neurons.

Previous studies with an HD model concluded that the deficiency of transcription factor XBP1 in CNS neurons had a neuroprotective effect in this disease, decreasing the amount of aggregates and improving neuronal viability. (This can be seen in the application examples).

In order to define the possible mechanisms underlying the protective effects observed in animals with XBP1 deficiency in the nervous system, a global profile analysis was conducted regarding the gene expression of 53 animals, including the striatum and cerebral cortex of XBP1-deficient mice, in a context of HD using Huntington model YAC128. From this study, IGF2 was obtained as the gene whose expression was most affected by XBP1 deletion, as seen in FIG. 1. In addition, it was the only one that coincided with a study conducted in parallel where the mRNA of XBP1-deficient mice was sequenced.

These results were confirmed by measuring by qPCR (quantitative PCR) the levels of Igf2 in different regions of the brain of XBP1-deficient mice. It was observed that the endogenous levels of Igf2 mRNA increased significantly in the cortex and in the striatum, as presented in FIG. 2, respectively. These data show that IGF2 is involved, in some way, in the protection observed in XBP1 KO mice.

In order to study the contribution of IGF2 to HD, its activity in cellular models that transiently express the polyQ79 peptide fused with GFP in Neuro2a cells was explored. The co-expression of IGF2 and polyQ79-GFP in Neuro2a cells drastically decreased the number of protein inclusions and aggregates according to the evaluation of three different methodologies, including fluorescent images, Western blot and filter trap, a technique that allows to evaluate large-size aggregates (FIGS. 3, 4 and 5, respectively).

Next, it was tested whether the observed effects were due to the secreted IGF2 or its intracellular accumulation. Thus, the peptide polyQ79 or mHTTQ85-GFP was expressed in Neuro2a cells in the presence of a medium enriched with IGF2. Consistently, IGF2 reduced the aggregates of polyQ and mHtt (FIGS. 6 and 7).

On the other hand, it was determined whether IGF2 was able to "undo" the pre-existing mHtt aggregates. To this end, Neuro2a cells that already express polyQ79-GFP or GFPmHTTQ85 were treated with an IGF2 enriched medium. As observed in previous experimental scenarios, IGF2 significantly decreased protein aggregation in both experimental parameters (FIGS. 8 and 9).

Altogether, the previously obtained results demonstrate a strong anti-aggregation effect in cell culture assays.

A natural continuation of the present development was the conduction of preliminary experiments in vivo, using an adeno-associated virus of AAV2/2 type (26). Within the sequence of this virus, a version of IGF2 marked with the HA epitope was cloned in order to better detect the expression of the peptide. In the first approach, viral particles expressing mHtt were injected in the presence or absence of IGF2. Two weeks later, the striatum of these animals was analyzed, observing a decrease in mutant huntingtin expression levels, as shown in FIG. 10.

In a more physiological approach, transgenic animals expressing mutated human huntingtin (YAC128 models) were treated. Neonatal animals of 1-2 days of age were injected intraventricularly with AAV-IGF2-HA. Six months later, the animals were sacrificed to obtain tissue. After treatment with AAV, a marked decrease in mHtt expression was observed in animals injected with IGF2-HA versus the control condition as shown in FIG. 11. Similarly, adult individuals were treated; these animals were injected with AAV-IGF2-HA at three months of age and sacrificed at six months of age to obtain tissue. As seen in FIG. 12, treatment with IGF2-HA reduced mHtt expression levels compared to the control condition.

Also, within said studies, some studies were conducted to verify motor improvement in mice with HD exposed to the AAV modified with IGF2, as shown in FIG. 13.

On the other hand, experiments were conducted where IGF2 levels were measured in protein extracts of caudate/putamen from HD patients and control individuals. The results showed that in patients with HD the content of IGF2 is hardly expressed, suggesting its implication in the development of the pathology. According to what is proposed in this patent, we consider that the present patent also achieves the restoration of IGF2 physiological levels, improving the symptomatology of the disease, as shown in FIG. 19.

With respect to the development of the adeno-associated virus (AAV), it comprises the viral recombinant genome comprising an expression cassette that includes a hippocampal tissue-specific transcriptional regulatory region operably linked to the polynucleotide of interest.

Adeno-associated viruses (AAV), in general, correspond to 42 serotypes and are derived from parvoviruses. In general, the different AAV serotypes are genomic sequences with a significant homology at amino acids and nucleic acids level, which provide identical genetic functions, provide vibrations that are essentially identical in functional and physical terms, and their replication and assembly use practically the same mechanisms.

Particularly, AAV serotype 2/2 having access number J01901.1 (AAV2/2) was used in the present invention, as presented in Table I (SEQ ID No. 1).

The AAV genome according to the present invention comprises a cis 5' actuator and an inverted terminal repeat sequence in 3', and an expression cassette. The ITR or LTR sequences are 141 base pairs long. Preferably, the entire sequence of the LTRs is used in the molecule and only slight modifications of the sequences are allowed. In a preferred embodiment of the present invention, the AAV recombinant genome comprises the 5' and 3' AAV LTRs.

On the other hand, ITRs can come from other AAV serotypes.

The AAV of the present invention comprises a capsid of any serotype. Particularly, for the present invention, the capsid derived from serotype 2 is preferred.

In some embodiments, an AAV cap for use in the method of the invention can be generated by mutagenesis (i.e., insertions, deletions, or substitutions) of one of the AAV caps or its encoding nucleic acids. In some embodiments, the AAV cap is at least 70%, 75%, 80%, 85%, 90%, 95%, 98%, or 99% A or more, similar to said AAV cap.

In some embodiments, the AAV cap is chimeric, it comprises the domains of two, three, four, or more of said AAV caps. In some embodiments, the AAV cap is a mosaic of monomers VP1, VP2, VP3, and derived from two or three different AAVs or a recombinant AAV (rAAV). In some embodiments, a rAAV composition comprises more than one of the aforementioned CAPS.

In some embodiments, an AAV CAP for use in a rAAV composition is designed to contain a heterologous sequence or other modification. For example, a peptide or protein sequence conferring selective targeting or immune evasion can be modified by genetic engineer into a Cap protein. Alternatively, or in addition, the Cap can be chemically modified so that the surface of the rAAV presents specific chemical modifications, for example, polyethylene glycol, which can facilitate immune evasion. The Cap protein can also be mutagenized (for example, to remove its natural binding receptor, or to mask an immunogenic epitope).

In one embodiment, the AAV vector contains a promoter with the addition of an Igf2 or Igf2-HA sequence of murine origin that can be selected from the following tables: Table IV (Igf2) (SEQ ID No. 4) and Table V (Igf2-HA) (SEQ ID No. 5), NCBI reference sequences NM_010514.3, NM_001122736.2, NM_001122737.2, NM_001315488.1, and NM 001315489.1, corresponding to transcriptional variants 1, 2, 3, 4, and 5 whose protein product is the same and is encoded by the sequence shown in the tables or sequence listing.

In one embodiment, the AAV vector contains a promoter with the addition of an Igf2 or Igf2-HA sequence of human origin that can be selected from the following table: Table VII (human Igf2) (SEQ ID No. 6), NCBI reference sequences NM_000612.5, NM_001007139.5, NM_001127598.2, NM_001291861.2, and NM_001291862.2 corresponding to the transcriptional variants 1, 2, 3, 4, and 5 whose protein product is the same and is encoded by the sequence represented in the table and sequence listing.

In one embodiment, the AAV vector contains a eukaryotic expression promoter with the addition of at least one Igf2 sequence, which can be selected from Table IV (SEQ ID No. 4), obtaining a sequence as shown in Table II (SEQ ID No. 2).

In one embodiment, the AAV vector contains a eukaryotic expression promoter with the addition of at least one Igf2-ha sequence that can be selected from Table V (SEQ ID No. 5), obtaining a sequence as shown in Table III (SEQ ID No. 3).

In one embodiment, the AAV vector contains a eukaryotic expression promoter with the addition of at least one human Igf2 sequence, which can be selected from Table VII (SEQ ID No. 6).

In one embodiment, the AAV vector contains a promoter with the addition of at least one sequence having 85% homology to a sequence selected from the aforementioned lists, Table II (SEQ ID No. 2) and Table III (SEQ ID No. 3).

In one embodiment, the AAV vector contains a promoter with the addition of at least one sequence having 70% homology to a sequence selected from the aforementioned tables.

In one embodiment, the AAV vector contains a promoter with the addition of at least one sequence that is a functional equivalent to a sequence selected from the aforementioned tables.

The transcriptional regulatory region may comprise a promoter and, optionally, an enhancer region. Preferably, the promoter is a eukaryotic gene expression promoter, selected from the following list: CAG (CAG is a promoter that contains sequences corresponding to the cytomegalovirus (CMV) immediate-early enhancer element, the promoter, the first exon, and the first intron of the chicken beta-actin gene, and the splicing acceptor of the rabbit beta-globin gene), CMV, b-globin, CBA, elFalpha, among others. The enhancer does not need to be specific for neuronal tissue.

In one embodiment, the promoter is specific, it is the cytomegalovirus or CMV promoter.

In one embodiment, the promoter is specific, it is b-globin.

In one embodiment, the promoter is specific, it is CAG.

In one embodiment, the promoter is specific, it is human elongation Factor-1 alpha, also known as elFalpha.

In another embodiment, the expression cassette forming part of the AAV of the invention further comprises a post-transcriptional regulatory region. In a preferred embodiment, the post-transcriptional regulatory region is the Woodchuck hepatitis virus post-transcriptional region (WPRE) or functional variants and fragments thereof and the PPT-CTS or functional variants and fragments themselves. In a particular embodiment, the post-transcriptional regulatory region is WPRE.

The expression cassette forming part of the AAV according to the invention comprises a "polynucleotide of interest". In a preferred embodiment, the polynucleotide of interest encodes a protein that acts systemically. In another embodiment, the polynucleotide of interest encodes a protein that acts within a neuron. In a preferred embodiment, the protein acting within said neuron is IGF2, including any of its isoforms that vary in sub-cellular locations and including any of its isoforms labeled with any epitope.

The packaging size limit of AAV vectors is limited to the size of the wild-type AAV genome, which varies in size according to the AAV serotype (i.e., between 4087 to 4767). For example, wild-type AAV-2 has an approximate genome size of 4.7 kB. In some embodiments, the cloning capacity of the recombinant RNA vector may be limited, and a desired coding sequence may involve the complete replacement of 4.8 kilobases of the virus genome. Large-sized genes may, therefore, not be suitable for use in a standard recombinant AAV vector, in some cases. An average expert will appreciate that options are available in the art for overcoming a limited coding capability. For example, the AAV IRT of two genomes can hybridize to form head to tail concatemers, almost doubling the capacity of the vector. The insertion of the splice sites allows the removal of the ITR after transcription. Other options for overcoming a limited cloning capacity will be evident to an expert in the field.

Routes of Administration

Routes of administration of the virus are subject to its crossing the blood-brain barrier to infect target neurons.

In order to achieve this purpose, two routes of administration have been defined in the present invention.

The first of these routes is nasal (27); normally, medicines administered through nasal route can enter the blood to the general circulation, can penetrate the brain directly, or in some cases can follow both routes. However, many of the factors that control drug flow through each of these pathways are not completely defined. Generally, there are three routes by which a drug administered in the nasal cavity can travel. These routes (27) include direct entry into the systemic circulation through the nasal mucosa (28), entry into the olfactory bulb by axonal transport through the neurons, and direct entry into the brain (29). The evidence supporting the role of each of these routes for a variety of model substrates is summarized below for different types of viruses.

| Transport routes followed by several viral solutes through nasal administration | | | |
|---|---|---|---|
| | Solute | | |
| Virus | Animal Model | Route of Administration | Followed route |
| Hepatitis virus | Mouse | Nasal inoculation | Olfactory nerve |
| Herpes Simplex virus | Mouse | Nose drops | Direct, Systemic, Olfactory nerve |
| Encephalitis virus | Mouse | Nasal inoculation | Olfactory nerve |
| Pneumococcus | Mouse | Nose drops | Direct |

This table is not intended to be exhaustive in nature, but rather to emphasize that some of the solutes of different classes have shown to follow one or more pathways.

Other routes of administration into CNS cells include (28):

Direct injection into fluid spaces, such as the vitreous humor of the eye; or into the cerebrospinal fluid through different routes, intraventricular or intrathecal (**), for its delivery to the choroid plexus, the ependymal/meningeal layers, and from there in the adjacent brain through processes extending within these layers; and its crossing the blood-brain barrier or blood-tumor barriers by intra-arterial injection combined with a temporary osmotic or pharmacological disruption.

The term (**) intrathecal (intra+teca, "within a sheath") is an adjective that refers to something that occurs or is introduced into an anatomical space or potential space within a sheath, most commonly the arachnoid membrane of the brain or spinal cord.

Dose Calculation

According to Ulusoy et al (29), the titration of the vector requires a range between $10^9$ to $10^{13}$ copies of genome (CG) per ml with a dose tested between $10^{10}$-$10^{12}$ gc/ml. On the other hand, at any rate of dilution of vectors to titrate, they must have a low-medium range of $10^{11}$ gc/ml, which results in the disappearance of toxicity.

Dosage in Humans

Dose range in humans would be in the range between $10^9$ to $10^{30}$ viral units/Kg of weight, without restricting this range to the application in different age groups or with volumes of distribution modified by age or pathology.

The maximum concentration or level of a substance is found experimentally or by observation, and does not cause detectable adverse alterations in the morphology, functional capacity, growth, development, or life span of the target organisms, distinguishable from those observed in normal (control) organisms of the same species and strain, under defined conditions of exposure.

Application Method rAAV2 vectors were injected bilaterally into the striatum using a 5 µl Hamilton syringe equipped with a glass capillary with a tip diameter of about 60-80 microns. Two microliters of buffer containing the appropriate concentrations of viral particles were injected at a rate of 0.4 µl/minute. The needle is removed slowly 5 minutes after the injection is given.

This figure presents the set of outstanding genes whose expression varied in the study of gene expression performed in XBP1-deficient animals in the context of HD. Levels of Igf2, Mmp14, Lrp4, and Uhrf, changed in the different groups, both in the cortex and in the striatum, in transgenic mice with human mutant huntingtin (YAC128), in XBP1-deficient litters, and control animals.

An upregulation for the Igf2 gene is clearly seen, both in the cortex and in the striatum.

FIG. 2

Figures 1, 2:
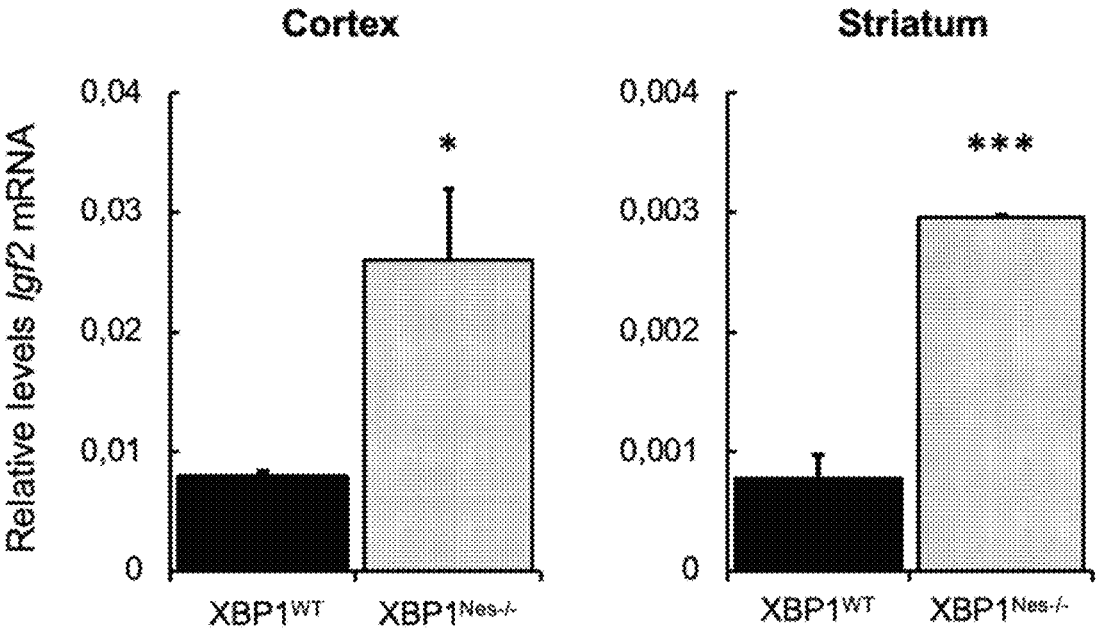
FIG. 1
Figure 3:
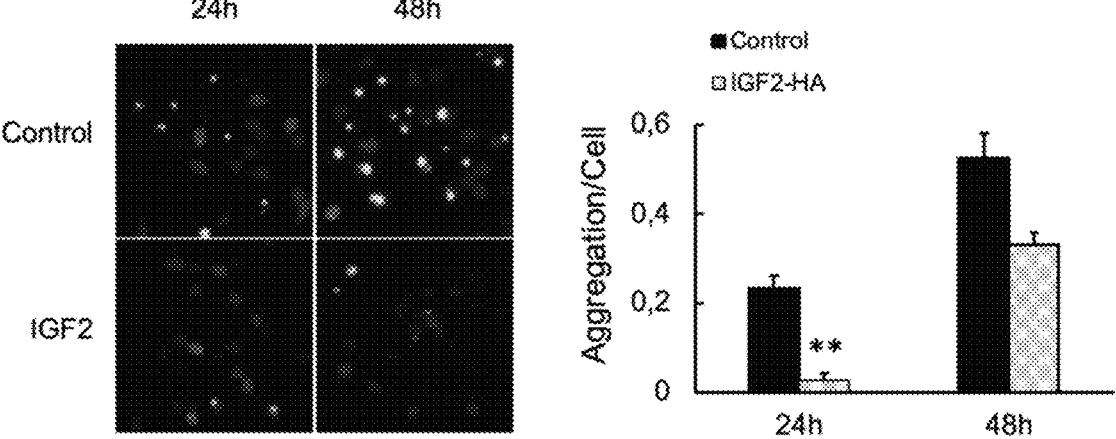
Figure 4:
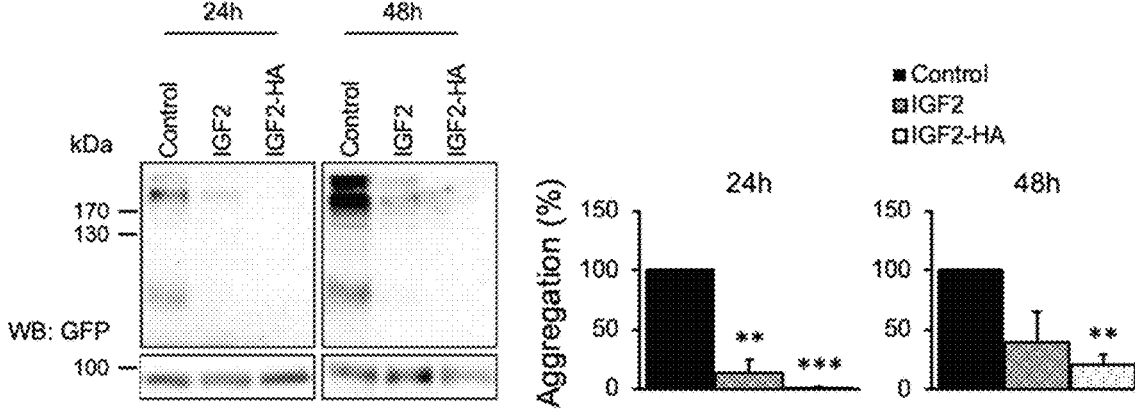
Figure 5:
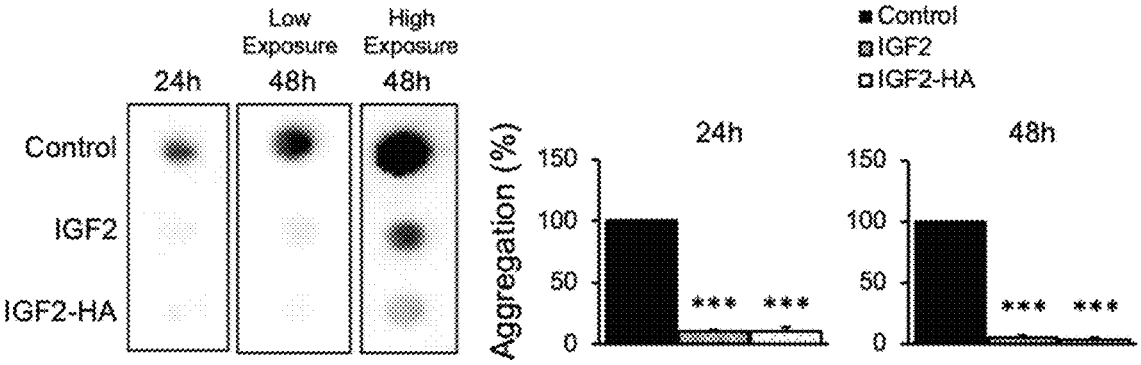
Figure 6:
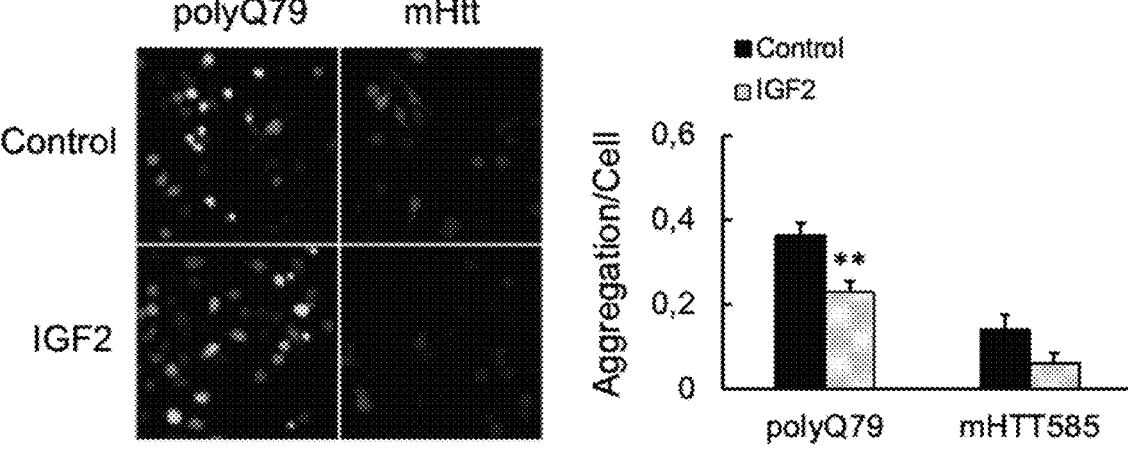
Figure 7:
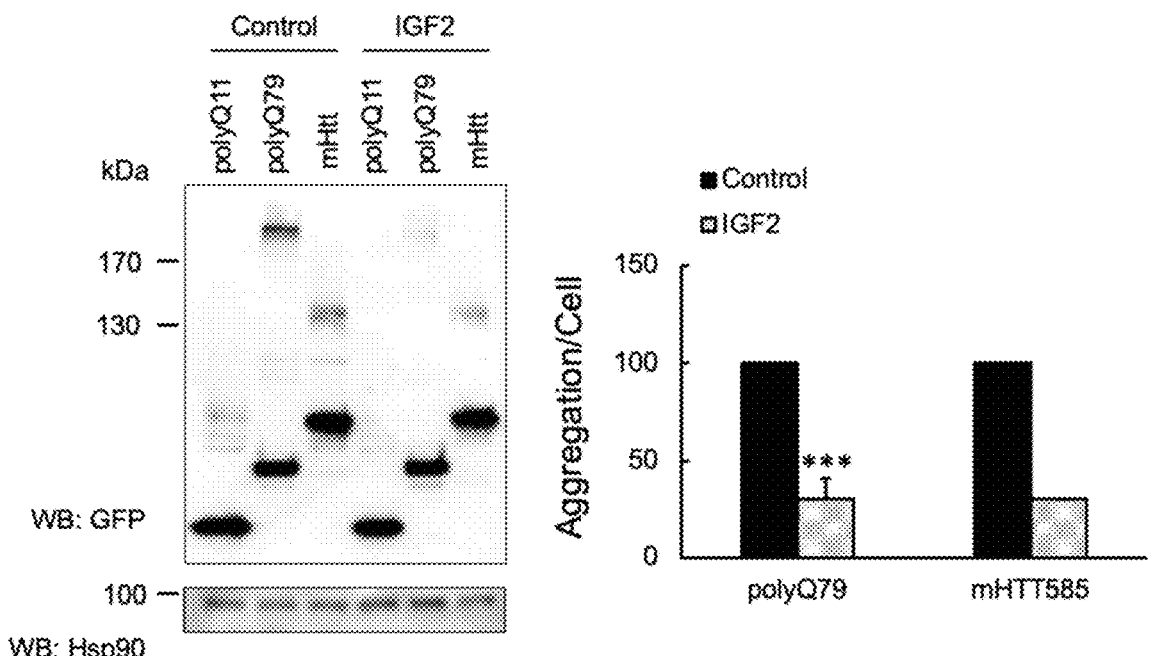
Figure 8:
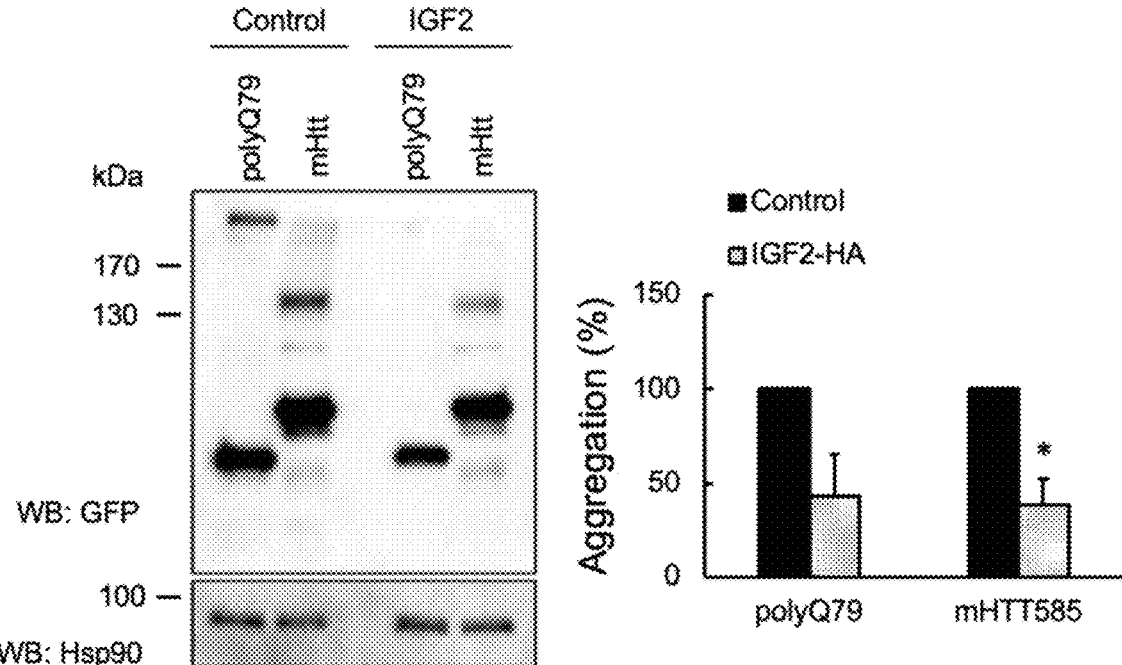
Figure 9:
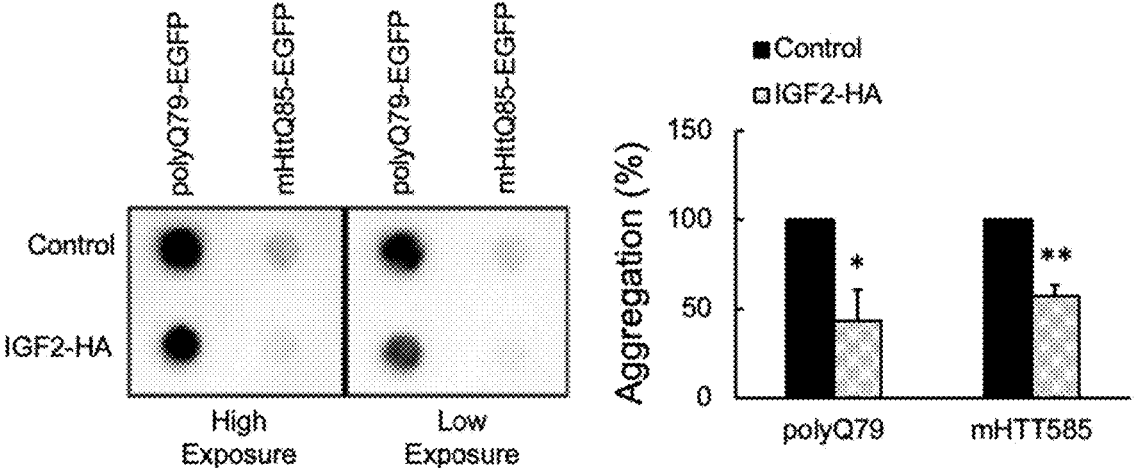

The results obtained in the study presented in FIG. 1 were confirmed by quantitative PCR (qPCR). This figure presents on the left results in cortex, and on the right results in striatum, the up-regulation of Igf2 mRNA in XBP1-deficient mice models in their brain. By this technique, it was observed that endogenous Igf2 mRNA levels are significantly increased in cortex and striatum in XBP1-deficient animals.

For all in vivo experiments, an n=5, t-student **p<0.05 was used.

FIG. 3

This figure shows how IGF2 expression decreases the levels of mHTT aggregates in a Neuro2a cell model for Huntington's disease.

Particularly, Neuro2a cells were transiently transfected with vectors for polyQ79-EGFP and IGF2 or control. Subsequently, the aggregation of polyQ was evaluated and quantified.

This figure presents the photograph by fluorescence microscopy and the quantification of said fluorescence to its right, at 24 and 48 hours after transfection.

For all in vivo experiments, an n=3, t-student ***p<0.001 was used.

FIG. 4

This figure shows how IGF2 expression decreases the levels of polyQ peptide aggregates in a Neuro2a cell model for Huntington's disease.

Particularly, Neuro2a cells were transiently transfected with vectors for polyQ79-EGFP and IGF2 or control. Subsequently, the aggregation of polyQ was evaluated and quantified.

This figure presents the photograph of the Western Blots and the quantification to its right, at 24 and 48 hours after transfection.

For all in vitro experiments, an n=3, t-student ***p<0.001 was used.

FIG. 5

This figure shows how IGF2 expression decreases the levels of polyQ peptide aggregates in a Neuro2a cell model for Huntington's disease.

Particularly, Neuro2a cells were transiently transfected with vectors for polyQ79-EGFP and IGF2 or control. Subsequently, the aggregation of polyQ was evaluated and quantified.

This figure presents the photograph of the filter trap and the quantification on its right, at 24 and 48 hours after transfection.

For all in vitro experiments, an n=3, t-student ***p<0.001 was used.

FIG. 6

This figure shows how IGF2 expression decreases the levels of mHTT aggregates in a Neuro2a cell model for Huntington's disease.

Particularly, Neuro2a cells were transiently transfected with vectors for polyQ79-EGFP, mHTTQ85-GFP in the presence of an IGF2-enriched medium or control. Protein aggregation was evaluated and quantified 24 hours later.

This figure presents the photograph by fluorescence microscopy and the quantification of that fluorescence on its right, after 24 hours of transfection.

For all in vitro experiments, an n=3, t-student ***p<0.001 was used.

FIG. 7

This figure shows how IGF2 expression decreases the levels of mHTT aggregates in a Neuro2a cell model for Huntington's disease.

Particularly, Neuro2a cells were transiently transfected with vectors for polyQ79-EGFP, mHTTQ85-GFP in the presence of an IGF2-enriched medium or control. Protein aggregation was evaluated and quantified 24 hours later.

This figure presents the photograph by Western Blot and the quantification on its right, after 24 hours of the transfection.

For all in vitro experiments, an n=3, t-student ***p<0.001 was used.

FIG. 8

This figure shows how IGF2 expression decreases the levels of mHTT aggregates in a Neuro2a cell model for Huntington's disease.

Particularly, in order to test whether IGF2 was able to reduce the previously formed inclusions of polyQ or mHTTQ85-GFP, cells expressing detectable inclusions were treated with an IGF2-enriched medium or control. Protein aggregation was evaluated and quantified 24 hours later.

This figure presents the photograph by Western Blot and its quantification on the right, after 24 hours of transfection.

For all in vitro experiments, an n=3, t-student ***p<0.001 was used.

FIG. 9

This figure shows how IGF2 expression decreases the levels of mHTT aggregates in a Neuro2a cell model for Huntington's disease.

Particularly, in order to test whether IGF2 was able to reduce the previously formed inclusions of polyQ or mHTTQ85-GFP, cells expressing detectable inclusions were treated with an IGF2-enriched medium or control. Protein aggregation was evaluated and quantified 24 hours later.

This figure presents the photograph of a filter trap and its quantification on the right, after 24 hours of the transfection.

For all in vitro experiments, an n=3, t-student ***p<0.001 was used.

FIG. 10

This figure shows how IGF2 expression decreases the levels of mHTT aggregates in a YAC128 murine model for Huntington's disease.

Particularly, wild animals were co-injected by stereotaxy into the striatum with AAVs that expressed a fragment of the mHtt with IGF2-HA or control. Protein aggregation of mHTT was evaluated and quantified 2 weeks later.

This figure presents the photograph of a Western Blot and its quantification on the right, after two weeks of transduction.

For all in vivo experiments, an n=5, t-student **p<0.05 was used.

FIG. 11

This figure shows how IGF2 expression from the AAV virus decreases the levels of the polyQ aggregates in a YAC128 murine model for Huntington's disease.

Particularly, AAVs expressing IGF2 or control were injected into the striatum of 90-day adult YAC128 mice. Three months after the injection, the levels of mHtt aggregation as well as DARPP-32 were evaluated as a reflection of the viability of the striatum neurons.

In a manner similar to that observed in vitro, there was a decrease in mHtt expression and an increase in DARPP levels, where this protein is representative of the viability of the neurons mainly affected by Huntington's disease. Therefore, it is concluded that the more DARPP there are, the less neuronal death happens.

For all in vivo experiments, an n=5, t-student **p<0.05 was used.

FIG. 12

This figure shows how IGF2 expression from the AAV virus decreases the levels of the polyQ aggregates in a YAC128 murine model for Huntington's disease.

Particularly, AAVs expressing IGF2 or control were injected intraventricularly in YAC128 neonatal animals of 1 or 2 days of age. Aggregation levels of mHtt were evaluated six months after the injection. In a manner similar to that observed in vitro, a decrease in mHtt expression was found.

FIG. 13

This figure shows how the expression of IGF2 in a YAC128 murine model for Huntington's disease manages to correct the motor problems generated by the disease.

Particularly, motor tests were performed on YAC128 mice bilaterally injected by stereotaxy with AAV-IGF2-HA or AAV-Control. Records were taken every two weeks, for two months. This figure presents a behavior graph in response to the Rotarod test over time under the effect of AAV2-IGF2-HA.

FIG. 14

The upper figure indicates the injection place in neonatal mice.

The lower figure shows the place where the AAVs are intra-cerebrally injected into the striatum of an adult mouse.

FIG. 15

The present figure shows a scheme of the AAV genome.

REP: Genes involved in the AAV replication mechanism.

VP: Genes involved in capsid formation and assembly.

ITR: It is the equivalent to LTR, inverted terminal repeated sequence.

FIG. 16

This figure presents the AAV virus vector with the IGF2-HA insert with the following specific description according to Table II (SEQ ID No. 2).

FIG. 17

This figure presents the AAV virus vector with the IGF2 insert with the following specific description according to Table III (SEQ ID No. 3).

FIG. 18

This figure presents the confirmation of the expression of the viral constructs generated. TO this end, HEK cells were transfected with the different constructs, after 24 hours of transfection, the proteins that were evaluated by WB were extracted using anti-IGF2 and anti-HA antibodies.

Finally, a band of the expected molecular weight for IGF2 (17 kDa) and IGF2-HA (18 kDa) is detected in the cells transfected with the plasmids pAAV-IGF2 and pAAV-IGF2-HA respectively.

FIG. 19

This figure shows the protein levels of IGF2 in patients with HD and with control individuals. It was found that in patients with HD, IGF2 is hardly expressed suggesting an involvement in the development of the pathology.

The figures on the left have a Western blot for IGF2, to the right of the figure shows the quantification of the brand and the marked low of it in patients with HD.

EXAMPLE OF APPLICATION

Experimental Test 1

Figure 14:
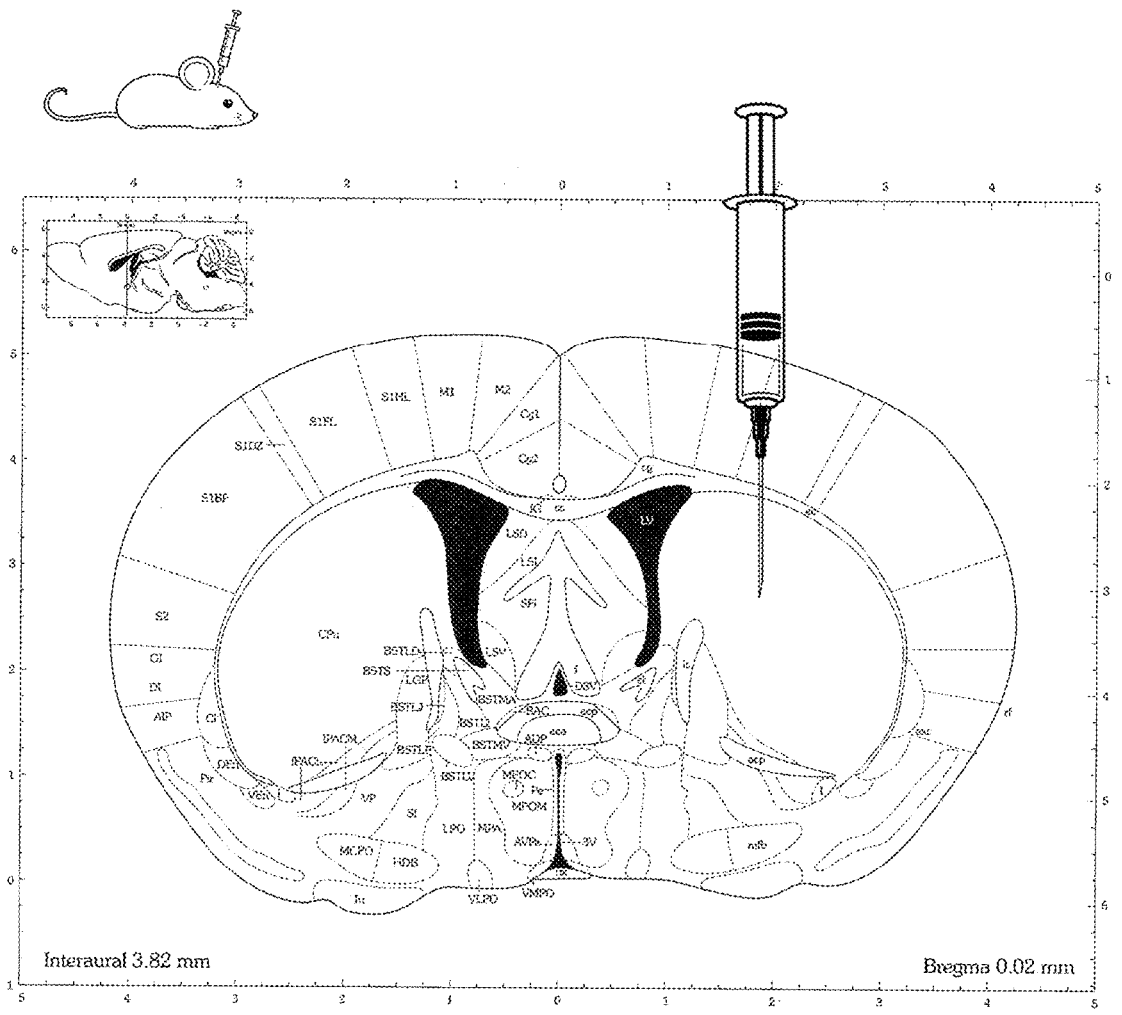
Figure 15:
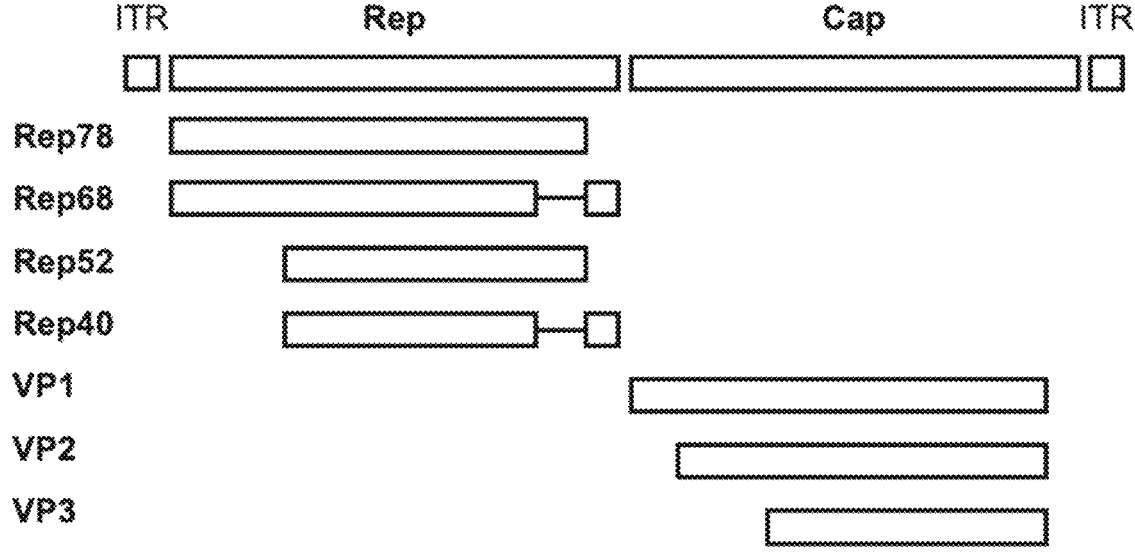
Figure 16:
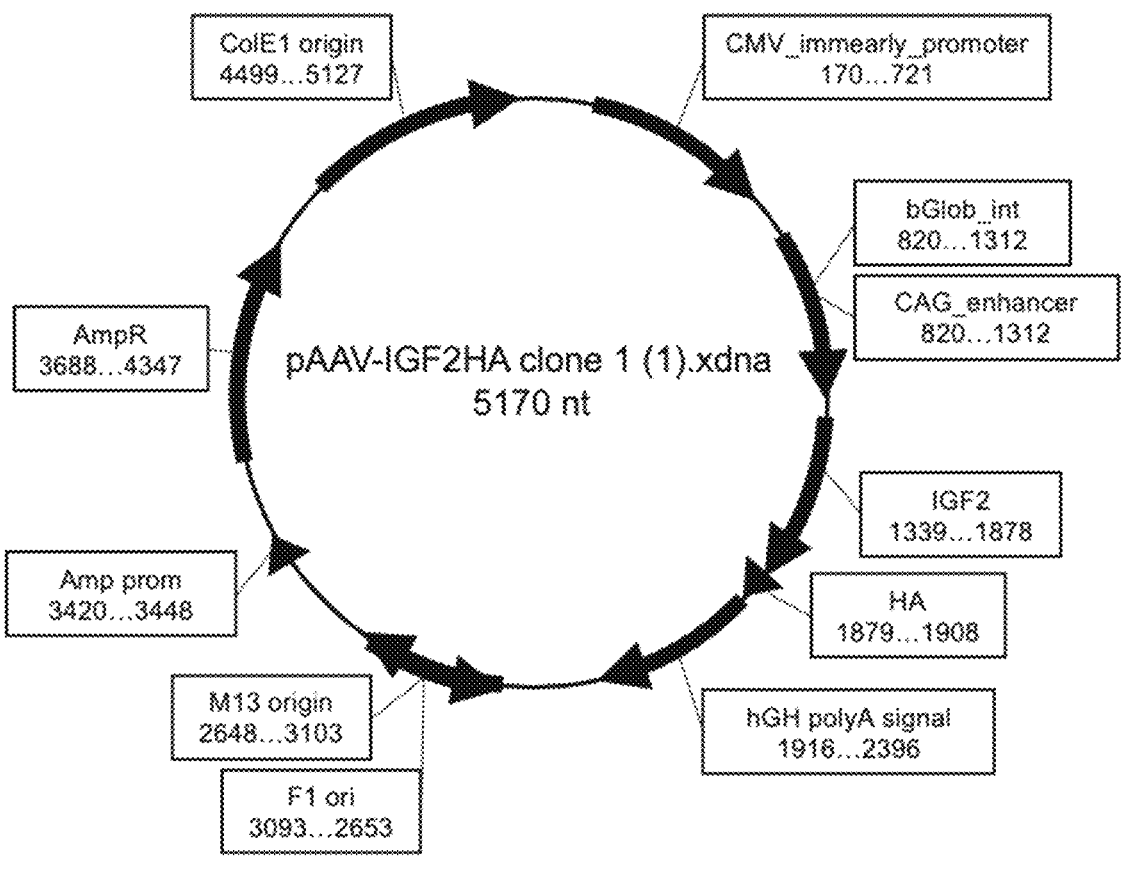
Figure 17:
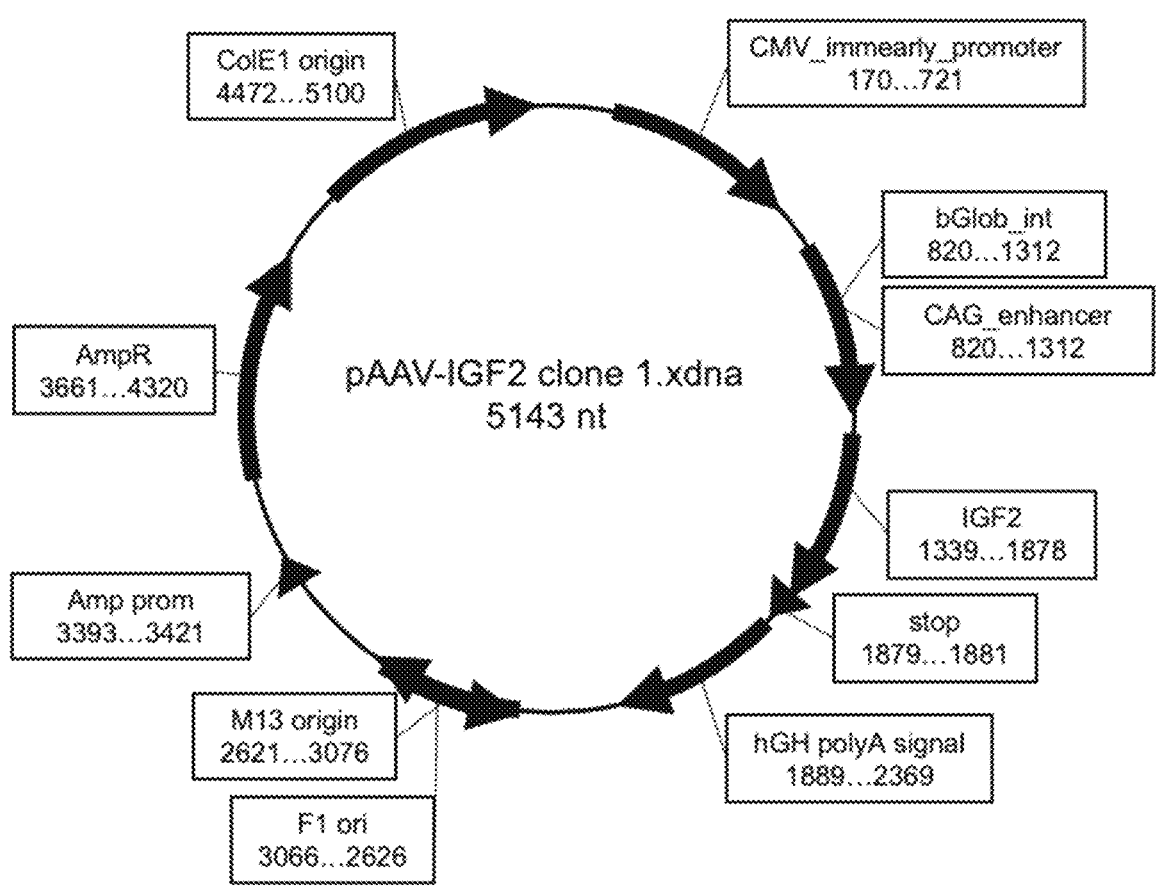

An in vivo experiment was performed in models of young adult WT mice. The AAV transformed virus expressing a large fragment of the human mHtt (588 bis) coupled to RFP and AAV/IGF2-HA or control was co-injected into the striatum by brain stereotaxy (FIG. 14).

Figure 10:
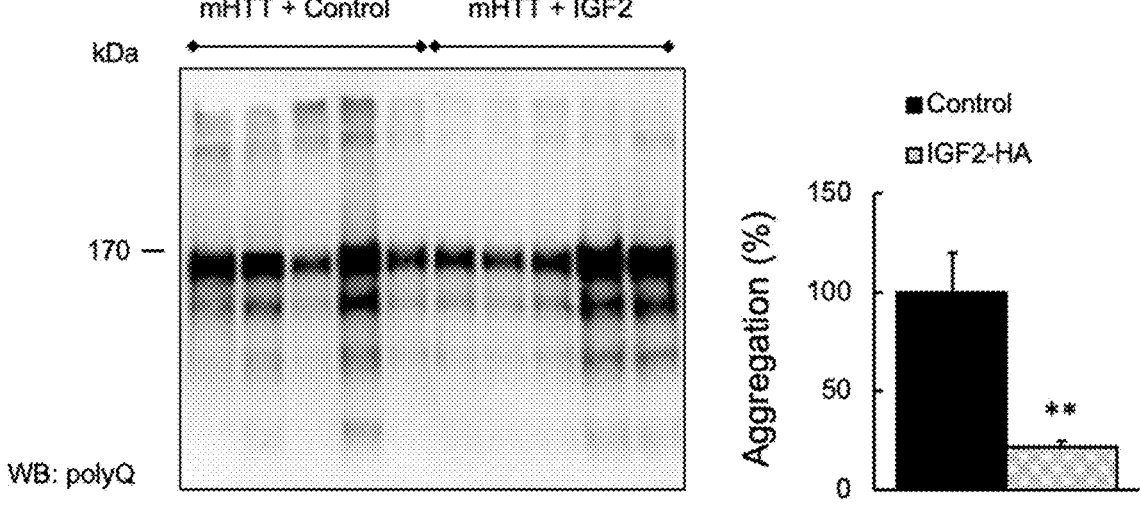

After two weeks, the animals were sacrificed and the striatum was dissected. As expected from previous in vitro results, a clear decrease in mHtt aggregation was observed after IGF2 administration (FIG. 10).

Experimental Test 2

In order to evaluate the effectiveness of IGF2 treatment, a more physiological model expressing human mHtt under its own promoter was used.

Figure 11:
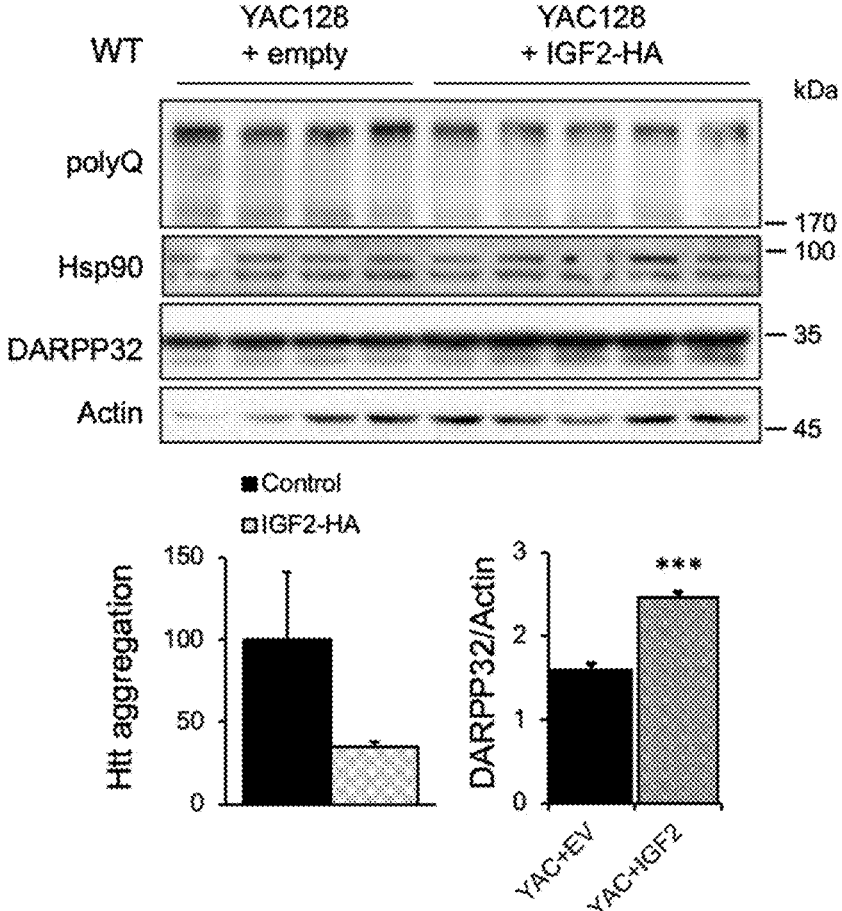
Figure 12:
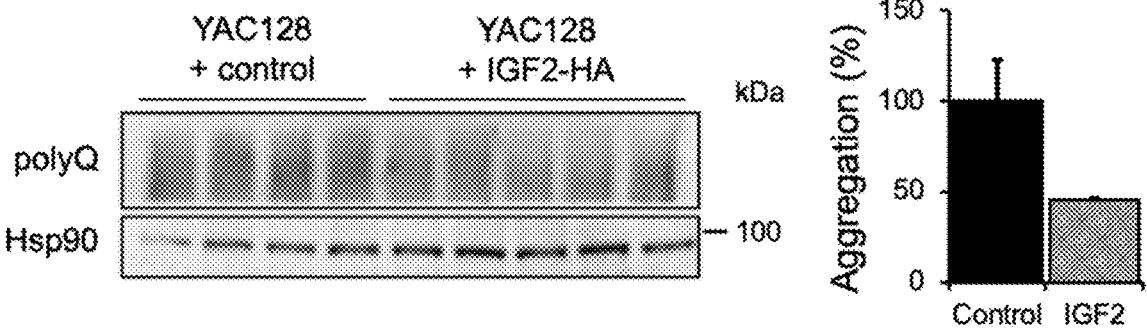

In this experimental strategy, it was demonstrated that treatment with AAV-IGF2 significantly decreased the levels of mutant huntingtin. In addition, greater neuronal viability was observed, as shown by the increase in DARPP32 levels (FIG. 11).

Particularly, it was tested whether the AAVs expressing IGF2-HA, compared to the control, injected by stereotactic surgery into the striatum, achieved the effect of decreasing the aggregation, thus improving neuronal viability.

Three months later, mHtt expression and DARPP-32 protein expression levels were evaluated and quantified.

A decrease in mHtt expression and an increase in DARPP levels were clearly observed, where this protein is representative of the viability of neurons mainly affected by Huntington's disease. Therefore, it was concluded that in the more DARPP there are, the less neuronal death happens.

For all in vivo experiments, at least one n=4, t-student **p<0.05 was used.

Experimental Test 3

Figure 13:
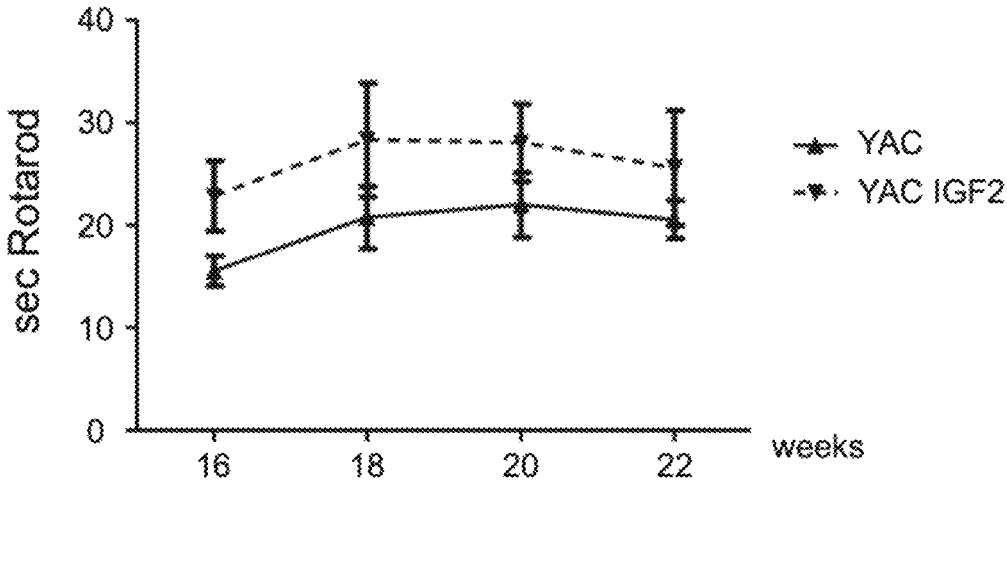

In this experiment, it was intended to study whether the treatment with AAV-IGF2-HA manages to correct the motor problems generated by the disease (FIG. 13). To this end, the animals were bilaterally injected by stereotaxy into the striatum with AAV-IGF2-HA or AAV-control.

For three months and every two weeks, they were subject to this motor test in order to quantify the progression of the disease. It was observed that the animals treated with AAV-IGF2-HA showed a better motor activity than their siblings treated with the AAV-control.

For all in vivo experiments, an n=5, t-student **p<0.05 was used.

Materials and Methods

Cell Cultures

Neuro2a cells are derived from a murine neuroblastoma and are widely used as cellular models. The cells were maintained in DMEM supplemented with 10% FBS, 100 U/ml glutamine penicillin, and 100 µg/ml streptomycin in a 5% $CO_2$ atmosphere at 37° C. The cells are stored frozen at −80° C. in 10% FBS DMSO in the case of N2a. For the maintenance of the line, passages were given every two or three days by trypsinizing the cells of the culture flasks, and after collecting the cells and centrifuging, they were reseeded in passes 1:3-1:6 according to the needs.

Cellular Transfections

Cell transfections were performed using the cationic reagent Effectene following the manufacturer's instructions.

Animals and Surgical Procedures:

Mice injected in adulthood were injected at 90 days of age. Mice injected in the neonate state were injected between postnatal days 1 and 2. According to the experiment, wild mice (WT) or YAC mice and their wild siblings were used as control. In all cases, the strain used was C57BL/6. Mice were kept in a 12:12 h light-dark cycle of and had free access to food and water.

For all animal experiments presented in the development of this invention, the guidelines established by the animal care and use committee at the University of Chile, Chile were used.

Generation of YAC 128 Transgenic Mice.

From a yeast artificial chromosome (YAC) that contained the complete human huntingtin gene, it was modified with an expansion of 128 glutamine repeats in exon 1. The resulting construct, YAC128, was injected into pronuclei of the FVB/N strain. Founding line number 53 was established as transgenic line. In order to obtain the c57BL/6 strain, backcrosses were made to ensure the animals background.

Immunoblot or "Western Blot".

The extraction of total proteins was done from cultures of N2a cells, or tissues dissected from wild or transgenic animals, as the case may be. The cells were harvested in 1% PBS-Triton buffer with protease and phosphatases inhibitors.

The samples were prepared at the desired concentration in loading buffer. Between 25 and 100 ug of protein were loaded in polyacrylamide gels. Electrophoresis was developed in a mini-Protean 3 system in glycine electrophoresis buffer. After the electrophoretic separation, the proteins were transferred to PVDF membranes previously hydrated in methanol and equilibrated for 5 minutes in transfer buffer, using a mini-Trans Blot system.

The filter trap assays were performed from the same protein extracts prepared in 1 SDS. Between 25-50 ug of protein were loaded onto the filter trap support using a membrane whose pore is <0.22 um.

Behavioral Tests

All experiments were conducted blind, and different animal cohorts were used for each behavioral test.

Rotarod

In summary, mice undergo a training of 4 days during which the animals make contact with the rotarod, the task and the experimenter. On day 5, the test is carried out measuring the time that the animal remains in the rotarod with an acceleration of 4 to 40 rpm in 120 s. The test continued until all the mice fell off the rod. The latency in falling and the rpm at the time of the fall were recorded for each mouse. Three assays were performed per mouse and averaged.

Production of Adeno-Associated Vectors

AAV Serotype 2 (AAV2/2) particles were produced by the transfection of 293-AAV cells (Agilent Technologies, Santa Clara, CA) and purified on a gradient of iodixanol followed by column affinity chromatography. The number of AAV particles containing the genome in the suspension, as well as the infectivity of the vector suspension in HEK293T cells were determined by TaqMan qPCR assays.

Preparation of the Adenoviral Plasmid (pAAV) for IGF2-HA

For the development of this objective, the murine IGF2 sequence was cloned into the adenoviral plasmid pAAV-MCS, which expresses the transgene under the CAG promoter. From the cDNA cloned in a pSPORT6 vector, kindly donated by Dr. Oliver Bracko, we performed PCRs that allowed us to obtain Igf2 and Igf2-HA to subclone into the pAAV-MCS vector. The IGF2-HA cDNA, which encodes HA-tagged C-terminus, was generated by PCR amplification of Igf2-EcoR1, SN2 and, Igf2-HA-Bgl II AS.

```
sense primer
                                    (SEQ ID No. 7)
5'GGCGAATTCCCTGGCTATGGGGATCCCAGTG3';

anti-sense-HA primer
                                    (SEQ ID No. 8)
5'ACGTAGATCTTTAGACGTAATCTGGAACATCGTATGGGTACTGATGGT
TGCTGG3' anti-sense primer
                                    (SEQ ID No. 9)
GGCAGATCTTCACTGATGGTTGCTGG
```

Due to the low efficiency of antibodies that recognize IGF2 in murine tissue, the sequence of the HA tag was included in the cloning strategy, which then allowed the identification of transduced cells and the expression of IGF2 (without excluding other epitope sequences to identify the cells transduced such as FLAG, GFP, His and Myc, among others). Therefore, IGF2 was amplified with the HA tag sequence at the 3' end. The obtained clones were confirmed by DNA sequencing. In this way, we generated the pAAV-CAG-IGF2-HA and pAAV-CAG-IGF2 constructs encoding (control) were made, with the following concentrations: $1.96 \times 10^{12}$, $1 \times 10^{13}$, and $1.2 \times 10^{13}$ units of transduction/$\rho\mu l$ respectively. 2 $\mu l$ of AAV were injected at a single point in the striatum region using a Hamilton syringe of 5 $\mu l$ (Hamilton, USA) in the following coordinates: AP: +0.07 cm, ML: −0.2 cm, DV: −0.31 cm (according to the atlas of Paxinos and Franklin, 1997). The injection was administered at a speed of 0.5 $\mu l$/min and the needle is left in place for 5 min before retraction of the needle. The mHTT expression was studied by WB as shown in FIG. 10. The IGF2 expression was verified by conventional PCR.

Preparation of Tissues for Biochemical Analysis

The mice were sacrificed by $CO_2$ narcosis, the brains were removed, and the cortex and striatum of both hemispheres were rapidly dissected on a plate on ice. The tissue was homogenized in phosphate buffered saline (PBS) (pH 7.4) supplemented with a mixture of protease and phosphatase inhibitors (Roche applied science, USA). The homogenate was divided to obtain mRNA and protein extraction was followed by standard purification and quantification protocols.

RNA Extraction, Real-Time PCR and Conventional PCR

Total RNA was isolated from the cortex and the striatum. After homogenization in PBS, Trizol RNA extraction protocol recommended by the manufacturer was followed. The cDNA was synthesized with a high capacity cDNA reverse transcription kit (Applied Biosystems). For the quantitative RT-PCR, Eva Green and the Mx3005P equipment from Stratagene were used. The relative amount of cDNA was calculated by means of comparative threshold cycle method with β-actin as a control. For the conventional PCR, we used the GoTaq® Green master mix from Promega. Primers sequences were obtained from PrimerBank (Table VI, SEQ ID No. 10 to SEQ ID No. 15).

TABLE VI

| Objective | Sense | Antisense |
|---|---|---|
| Igf2 | GTC GCA TGC TTG CCA AAG AG (SEQ ID NO. 10) | GGT GGT AAC ACG ATC AGG GG (SEQ ID NO. 11) |
| IGF2-HA | GTC GCA TGC TTG CCA AAG AG (SEQ ID NO. 12) | TAG ACG TAA TCT GGA ACA TCG (SEQ ID NO. 13) |
| ACTIN | TAC CAC CAT GTA CCC AGC A (SEQ ID NO. 14) | CTC AGG AGG AGC AAT GAT CTT GAT (SEQ ID NO. 15) | for the IGF2 fusion protein with and without the tag, respectively. The empty adenoviral plasmid pAAV CAG was used as a control.

In order to confirm the expression of the generated constructs, we transfected HEK cells with the different constructs, after 24 hours of transfection we performed the extraction of proteins that were evaluated by WB using anti-IGF2 and anti-HA antibodies.

Figure 18:
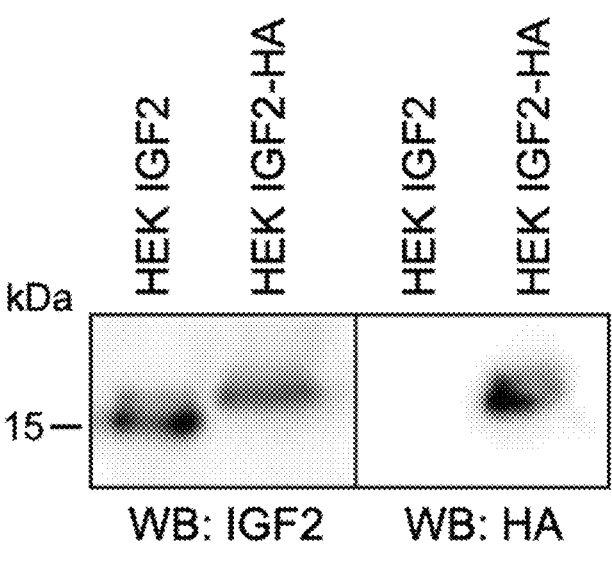
Figure 19:
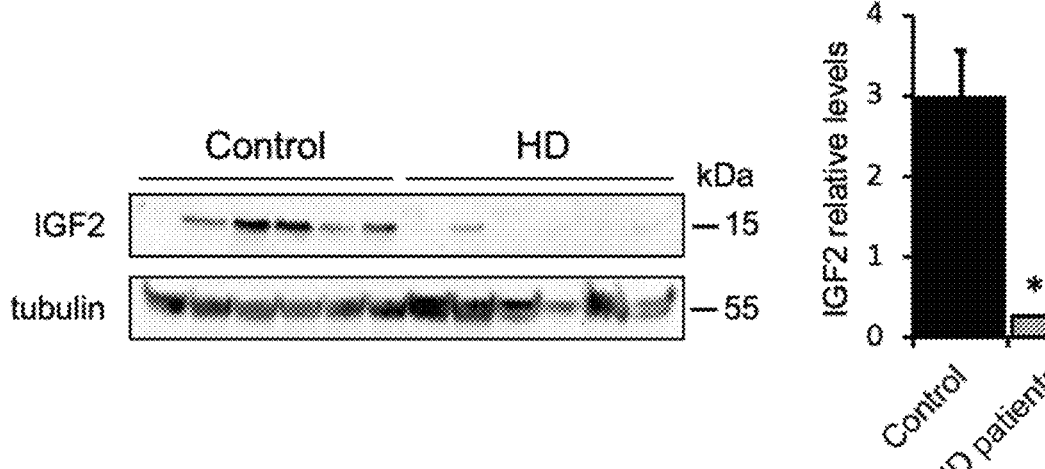

Finally, as shown in FIG. 18, we detected a band of the expected molecular weight for IGF2 (17 kDa) and IGF2-HA (18 kDa) in cells transfected with the plasmids pAAV-IGF2 and pAAV-IGF2-HA respectively.

Stereotactic Injections

Mice were anesthetized using ketamine/xylazine anesthesia (Ketamine: 100 mg/kg, xylazine: 10 mg/kg, Vetcom, Chile), and placed on a stereotaxic frame with their mouths, noses and ears fastened (David Kopf Instruments, USA). According to the experiment, unilateral or bilateral injections of AAV-mHTT-RFP, AAV-IGF2-HA, or AAV-empty Western Blot Protein extraction from mouse tissue was carried out in RIPA buffer (20 mM Tris pH 8.0, 150 mM NaCl, 0.1% SDS, 0.5% deoxycholate, 0.5% Triton X-100) containing a mixture of protease inhibitors and a mixture of phosphatase inhibitors (Sigma, USA). The extraction of proteins from cell lines was carried out in 1% Triton in PBS containing of protease and phosphatase inhibitors. The samples were quantified with the BCA assay kit (Pierce, USA). Total cellular extracts were separated by SDS-PAGE and transferred to polyvinylidene difluoride membranes. The following antibodies were used for the immunoblot analysis: anti-Hsp90 (1:3000, Santa Cruz), anti-IGF2 (1:1000 Abcam), anti-polyQ (1:1000 Sigma), anti-GFP (1:1000 Santa Cruz), anti-DARPP32 (1:1000 Cell Siganlling), anti-tubulin (1:3000, Millipore).

Neuronal Cultures and Transfections

Neuro2A cells were obtained from the ATCC and cultured in DMEM medium supplemented with 5% bovine serum and antibiotics (10000 U/ml penicillin, 10 mg/ml strepto-mycin), at 37° C. and 5% $CO_2$.

Statistics

The data are expressed as mean and SEM. Based on the experiments, the results were statistically compared using the Student's T test or the Mann-Whitney test, two-way ANOVA followed by Holm-Sidak or Bonferroni as a post-hoc test or Kruskal-Wallis, one-way ANOVA in ranges followed by the Dunn or Bonferroni Method as a post-hoc test.

REFERENCES

1. W. E. Balch, R. I. Morimoto, A. Dillin, J. W. Kelly, Science. 319, 916-919 (2008).
2. J. Leitman et al., PLoS One. 9, e90803 (2014).
3. H. Lee et al., Hum. Mol. Genet. 21, 101-114 (2012).
4. J. R. Naranjo et al., J. Clin. Invest. 126, 627-638 (2016).
5. R. L. Vidal et al., Hum Mol Genet. 21, 2245-2262 (2012).
6. R. Vidal, B. Caballero, A. Couve, C. Hetz, Curr. Mol. Med. 11, 1-12 (2011).
7. C. Hetz, B. Mollereau, Nat Rev Neurosci. 15, 233-249 (2014).
8. H. L. Smith, G. R. Mallucci, Brain (2016), doi:10.1093/brain/aww101.
9. W. Scheper, J. J. M. Hoozemans, Acta Neuropathol. 130, 315-31 (2015).
10. P. Walter, D. Ron, Science (80-.). 334, 1081-1086 (2011).
11. C. Hetz et al., Genes Dev. 23, 2294-2306 (2009).
12. P. Valdes et al., Proc. Natl. Acad. Sci. U.S.A 111, 6804-9 (2014).
13. A. M. Fernandez, I. Torres-Alemán, Nat. Rev. Neurosci. 13, 225-239 (2012).
14. E. Carro et al., Neurobiol. Aging. 27, 1250-1257 (2006).

15. B. K. Kaspar, J. Lladó, N. Sherkat, et al, Science. 301, 839-42 (2003).
16. C. K. Franz et al., Neurobiol. Dis. 33, 473-81 (2009).
17. M. Pascual-Lucas et al., EMBO Mol. Med. 6, 1246-1263 (2014).
18. T. J. Mellott, S. M. Pender, R. M. Burke, et al, PLoS One. 9, e94287 (2014).
19. I. Allodi et al., Sci. Rep. 6, 25960 (2016).
20. E. J. Rivera et al., J. Alzheimers. Dis. 8, 247-68 (2005).
21. W. E. Heywood et al., Mol. Neurodegener. 10, 64 (2015).
22. D. Åberg et al., J. Alzheimers. Dis. 48, 637-46 (2015).
23. P. Garcia-Huerta, P. Troncoso-Escudero, C. Jerez, C. Hetz, R. L. Vidal, Brain Res. (2016), doi:10.1016/j.brainres.2016.02.052.
24. Fauli Trillo C, "Tratado de Farmacia Galénica" (Ed Luzán 5, SA, Madrid, E S, 1993.) and Gennaro A, Ed., "Remington: The Science and Practice de Farmacia" 20a ed. (Lippincott Williams Wilkins, Philadelphia, PA, Estados Unidos, 2003).
25. Product Data Sheet Paav-MCS Expression vector, Catalog Number: VPK-410.
26. A. Zuleta, R. L. Vidal, D. Armentano, G. Parsons, C. Hetz, Biochem Biophys Res Commun. 420, 558-563 (2012).
27. Candace et al (2005) Journal of Pharmaceutical Sciences, volume 94 number (6), pages 1187-1195.
28. Constantini et al (2000) Gene Therapy volume 7, pages 93-10.
29. Ulusoy et al (1999) Molecular Theraphy volume 17, no 9, pages 1574-1584.
30. Carter B, asociados-A.deno para la entrega de genes, Lassic D, et al, Eds, "Gene" Therapy: Mecanismos y estrategias terapéuticas" . . . (Marcel Dekker, Inc., Nueva York, NY, Estados Unidos, 2000) and Gao et al., J. Virol. 2004; 78 (12): 6381-6388.

TABLE I

Characteristics and sequence of pAAV/2-MCS plasmid.
GenBank: AF043303.1
Origin

| | |
|---|---|
| 1 | TTGGCCACTC CCTCTCTGCG CGCTCGCTCG CTCACTGAGG CCGGGCGACC AAAGGTCGCC |
| 61 | CGACGCCCGG GCTTTGCCCG GGCGGCCTCA GTGAGCGAGC GAGCGCGCAG AGAGGGAGTG |
| 121 | GCCAACTCCA TCACTAGGGG TTCCTGGAGG GGTGGAGTCG TGACGTGAAT TACGTCATAG |
| 181 | GGTTAGGGAG GTCCTGTATT AGAGGTCACG TGAGTGTTTT GCGACATTTT GCGACACCAT |
| 241 | GTGGTCACGC TGGGTATTTA AGCCCGAGTG AGCACGCAGG GTCTCCATTT TGAAGCGGGA |
| 301 | GGTTTGAACG CGCAGCCGCC ATGCCGGGGT TTTACGAGAT TGTGATTAAG GTCCCCAGCG |
| 361 | ACCTTGACGA GCATCTGCCC GGCATTTCTG ACAGCTTTGT GAACTGGGTG GCCGAGAAGG |
| 421 | AATGGGAGTT GCCGCCAGAT TCTGACATGG ATCTGAATCT GATTGAGCAG GCACCCCTGA |
| 481 | CCGTGGCCGA GAAGCTGCAG CGCGACTTTC TGACGGAATG GCGCCGTGTG AGTAAGGCCC |
| 541 | CGGAGGCCCT TTTCTTTGTG CAATTTGAGA AGGGAGAGAG CTACTTCCAC ATGCACGTGC |
| 601 | TCGTGGAAAC CACCGGGGTG AAATCCATGG TTTTGGGACG TTTCCTGAGT CAGATTCGCG |
| 661 | AAAAACTGAT TCAGAGAATT TACCGCGGGA TCGAGCCGAC TTTGCCAAAC TGGTTCGCGG |
| 721 | TCACAAAGAC CAGAAATGGC GCCGGAGGCG GGAACAAGGT GGTGGATGAG TGCTACATCC |
| 781 | CCAATTACTT GCTCCCCAAA ACCCAGCCTG AGCTCCAGTG GGCGTGGACT AATATGGAAC |
| 841 | AGTATTTAAG CGCCTGTTTG AATCTCACGG AGCGTAAACG GTTGGTGGCG CAGCATCTGA |
| 901 | CGCACGTGTC GCAGACGCAG GAGCAGAACA AAGAGAATCA GAATCCCAAT TCTGATGCGC |

TABLE I-continued

```
 961    CGGTGATCAG ATCAAAAACT TCAGCCAGGT ACATGGAGCT GGTCGGGTGG CTCGTGGACA

1021    AGGGGATTAC CTCGGAGAAG CAGTGGATCC AGGAGGACCA GGCCTCATAC ATCTCCTTCA

1081    ATGCGGCCTC CAACTCGCGG TCCCAAATCA AGGCTGCCTT GGACAATGCG GGAAAGATTA

1141    TGAGCCTGAC TAAAACCGCC CCCGACTACC TGGTGGGCCA GCAGCCCGTG GAGGACATTT

1201    CCAGCAATCG GATTTATAAA ATTTTGGAAC TAAACGGGTA CGATCCCCAA TATGCGGCTT

1261    CCGTCTTTCT GGGATGGGCC ACGAAAAAGT TCGGCAAGAG GAACACCATC TGGCTGTTTG

1321    GGCCTGCAAC TACCGGGAAG ACCAACATCG CGGAGGCCAT AGCCCACACT GTGCCCTTCT

1381    ACGGGTGCGT AAACTGGACC AATGAGAACT TTCCCTTCAA CGACTGTGTC GACAAGATGG

1441    TGATCTGGTG GGAGGAGGGG AAGATGACCG CCAAGGTCGT GGAGTCGGCC AAAGCCATTC

1501    TCGGAGGAAG CAAGGTGCGC GTGGACCAGA AATGCAAGTC CTCGGCCCAG ATAGACCCGA

1561    CTCCCGTGAT CGTCACCTCC AACACCAACA TGTGCGCCGT GATTGACGGG AACTCAACGA

1621    CCTTCGAACA CCAGCAGCCG TTGCAAGACC GGATGTTCAA ATTTGAACTC ACCCGCCGTC

1681    TGGATCATGA CTTTGGGAAG GTCACCAAGC AGGAAGTCAA AGACTTTTTC CGGTGGGCAA

1741    AGGATCACGT GGTTGAGGTG GAGCATGAAT TCTACGTCAA AAAGGGTGGA GCCAAGAAAA

1801    GACCCGCCCC CAGTGACGCA GATATAAGTG AGCCCAAACG GGTGCGCGAG TCAGTTGCGC

1861    AGCCATCGAC GTCAGACGCG GAAGCTTCGA TCAACTACGC AGACAGGTAC CAAAACAAAT

1921    GTTCTCGTCA CGTGGGCATG AATCTGATGC TGTTTCCCTG CAGACAATGC GAGAGAATGA

1981    ATCAGAATTC AAATATCTGC TTCACTCACG GACAGAAAGA CTGTTTAGAG TGCTTTCCCG

2041    TGTCAGAATC TCAACCCGTT TCTGTCGTCA AAAAGGCGTA TCAGAAACTG TGCTACATTC

2101    ATCATATCAT GGGAAAGGTG CCAGACGCTT GCACTGCCTG CGATCTGGTC AATGTGGATT

2161    TGGATGACTG CATCTTTGAA CAATAAATGA TTTAAATCAG GTATGGCTGC CGATGGTTAT

2221    CTTCCAGATT GGCTCGAGGA CACTCTCTCT GAAGGAATAA GACAGTGGTG GAAGCTCAAA

2281    CCTGGCCCAC CACCACCAAA GCCCGCAGAG CGGCATAAGG ACGACAGCAG GGGTCTTGTG

2341    CTTCCTGGGT ACAAGTACCT CGGACCCTTC AACGGACTCG ACAAGGGAGA GCCGGTCAAC

2401    GAGGCAGACG CCGCGGCCCT CGAGCACGAC AAAGCCTACG ACCGGCAGCT CGACAGCGGA

2461    GACAACCCGT ACCTCAAGTA CAACCACGCC GACGCGGAGT TTCAGGAGCC CCTTAAAGAA

2521    GATACGTCTT TTGGGGGCAA CCTCGGACGA GCAGTCTTCC AGGCGAAAAA GAGGGTTCTT

2581    GAACCTCTGG GCCTGGTTGA GGAACCTGTT AAGACGGCTC CGGGAAAAAA GAGGCCGGTA

2641    GAGCACTCTC CTGTGGAGCC AGACTCCTCC TCGGGAACCG GAAAGGCGGG CCAGCAGCCT

2701    GCAAGAAAAA GATTGAATTT TGGTCAGACT GGAGACGCAG ACTCAGTACC TGACCCCCAG

2761    CCTCTCGGAC AGCCACCAGC AGCCCCCTCT GGTCTGGGAA CTAATACGAT GGCTACAGGC

2821    AGTGGCGCAC CAATGGCAGA CAATAACGAG GGCGCCGACG GAGTGGGTAA TTCCTCGGGA

2881    AATTGGCATT GCGATTCCAC ATGGATGGGC GACAGAGTCA TCACCACCAG CACCCGAACC

2941    TGGGCCCTGC CCACCTACAA CAACCACCTC TACAAACAAA TTTCCAGCCA ATCAGGAGCC

3001    TCGAACGACA ATCACTACTT TGGCTACAGC ACCCCTTGGG GGTATTTTGA CTTCAACAGA

3061    TTCCACTGCC ACTTTTCACC ACGTGACTGG CAAAGACTCA TCAACAACAA CTGGGGATTC

3121    CGACCCAAGA GACTCAACTT CAAGCTCTTT AACATTCAAG TCAAAGAGGT CACGCAGAAT

3181    GACGGGTACG ACGACGATTGC CAATAACCTT ACCAGCACGG TTCAGGTGTT TACTGACTCG

3241    GAGTACCAGC TCCCGTACGT CCTCGGCTCG GCGCATCAAG GATGCCTCCC GCCGTTCCCA

3301    GCAGACGTCT TCATGGTGCC ACAGTATGGA TACCTCACCC TGAACAACGG GAGTCAGGCA
```

TABLE I-continued

```
3361    GTAGGACGCT CTTCATTTTA CTGCCTGGAG TACTTTCCTT CTCAGATGCT GCGTACCGGA

3421    AACAACTTTA CCTTCAGCTA CACTTTTGAG GACGTTCCTT TCCACAGCAG CTACGCTCAC

3481    AGCCAGAGTC TGGACCGTCT CATGAATCCT CTCATCGACC AGTACCTGTA TTACTTGAGC

3541    AGAACAAACA CTCCAAGTGG AACCACCACG CAGTCAAGGC TTCAGTTTTC TCAGGCCGGA

3601    GCGAGTGACA TTCGGGACCA GTCTAGGAAC TGGCTTCCTG GACCCTGTTA CCGCCAGCAG

3661    CGAGTATCAA AGACATCTGC GGATAACAAC AACAGTGAAT ACTCGTGGAC TGGAGCTACC

3721    AAGTACCACC TCAATGGCAG AGACTCTCTG GTGAATCCGG GCCCGGCCAT GGCAAGCCAC

3781    AAGGACGATG AAGAAAGTT TTTTCCTCAG AGCGGGGTTC TCATCTTTGG GAAGCAAGGC

3841    TCAGAGAAAA CAAATGTGGA CATTGAAAAG GTCATGATTA CAGACGAAGA GGAAATCAGG

3901    ACAACCAATC CCGTGGCTAC GGAGCAGTAT GGTTCTGTAT CTACCAACCT CCAGAGAGGC

3961    AACAGACAAG CAGCTACCGC AGATGTCAAC ACACAAGGCG TTCTTCCAGG CATGGTCTGG

4021    CAGGACAGAG ATGTGTACCT TCAGGGGCCC ATCTGGGCAA AGATTCCACA CACGGACGGA

4081    CATTTTCACC CCTCTCCCCT CATGGGTGGA TTCGGACTTA AACACCCTCC TCCACAGATT

4141    CTCATCAAGA ACACCCCGGT ACCTGCGAAT CCTTCGACCA CCTTCAGTGC GGCAAAGTTT

4201    GCTTCCTTCA TCACACAGTA CTCCACGGGA CAGGTCAGCG TGGAGATCGA GTGGGAGCTG

4261    CAGAAGGAAA ACAGCAAACG CTGGAATCCC GAAATTCAGT ACACTTCCAA CTACAACAAG

4321    TCTGTTAATG TGGACTTTAC TGTGGACACT AATGGCGTGT ATTCAGAGCC TCGCCCCATT

4381    GGCACCAGAT ACCTGACTCG TAATCTGTAA TTGCTTGTTA ATCAATAAAC CGTTTAATTC

4441    GTTTCAGTTG AACTTTGGTC TCTGCGTATT TCTTTCTTAT CTAGTTTCCA TGGCTACGTA

4501    GATAAGTAGC ATGGCGGGTT AATCATTAAC TACAAGGAAC CCCTAGTGAT GGAGTTGGCC

4561    ACTCCCTCTC TGCGCGCTCG CTCGCTCACT GAGGCCGGGC GACCAAAGGT CGCCCGACGC

4621    CCGGGCTTTG CCCGGGCGGC CTCAGTGAGC GAGCGAGCGC GCAGAGAGGG AGTGGCCAA
```

| TABLE II | TABLE II-continued |
|---|---|
| pAAV2-IGF2 vector sequence | pAAV2-IGF2 vector sequence |

CCTGCAGGCAGCTGCGCGCTCGCTCGCTCACTGAGGCCGCCCGGGCAAA
GCCCGGGCGTCGGGCGACCTTTGGTCGCCCGGCCTCAGTGAGCGAGCGA
GCGCGCAGAGAGGGAGTGGCCAACTCCATCACTAGGGGTTCCTGCGGCC
GCACGCGTGGAGCTAGTTATTAATAGTAATCAATTACGGGGTCATTAGT
TCATAGCCCATATATGGAGTTCCGCGTTACATAACTTACGGTAAATGGC
CCGCCTGGCTGACCGCCCAACGACCCCCGCCCATTGACGTCAATAATGA
CGTATGTTCCCATAGTAACGTCAATAGGGACTTTCCATTGACGTCAATG
GGTGGAGTATTTACGGTAAACTGCCCACTTGGCAGTACATCAAGTGTAT
CATATGCCAAGTACGCCCCCTATTGACGTCAATGACGGTAAATGGCCCG
CCTGGCATTATGCCCAGTACATGACCTTATGGGACTTTCCTACTTGGCA
GTACATCTACGTATTAGTCATCGCTATTACCATGGTGATGCGGTTTTGG
CAGTACATCAATGGGCGTGGATAGCGGTTTGACTCACGGGGATTTCCAA
GTCTCCACCCCATTGACGTCAATGGGAGTTTGTTTTGCACCAAAATCAA
CGGGACTTTCCAAAATGTCGTAACAACTCCGCCCCATTGACGCAAATGG
GCGGTAGGCGTGTACGGTGGGAGGTCTATATAAGCAGAGCTCGTTTAGT
GAACCGTCAGATCGCCTGGAGACGCCATCCACGCTGTTTTGACCTCCAT
AGAAGACACCGGGACCGATCCAGCCTCCGCGGATTCGAATCCCGGCCGG
GAACGGTGCATTGGAACGCGGATTCCCCGTGCCAAGAGTGACGTAAGTA
CCGCCTATAGAGTCTATAGGCCCACAAAAAATGCTTTCTTCTTTTAATA
TACTTTTTTGTTTATCTTATTTCTAATACTTTCCCTAATCTCTTTCTTT
CAGGGCAATAATGATACAATGTATCATGCCTCTTTGCACCATTCTAAAG
AATAACAGTGATAATTTCTGGGTTTAAGGCAATAGCAATATTTCTGCATA
TAAATATTTCTGCATATAAATTGTAACTGATGTAAGAGGTTTCATATTG
CTAATAGCAGCTACAATCCAGCTACCATTCTGCTTTTATTTTATGGTTG
GGATAAGGCTGGATTATTCTGAGTCCAAGCTAGGCCCTTTTGCTAATCA
TGTTCATACCTCTTATCTTCCTCCCACAGCTCCTGGGCAACGTGCTGGT
CTGTGTGCTGGCCCATCACTTTGGCAAAGAATTGGGATTCGAACATCGA
TTGAATTCCCTGGCTATGGGGATCCCAGTGGGGAAGTCGATGTTGGTGC

TTCTCATCTCTTTGGCCTTCGCCTTGTGCTGCATCGCTGCTTACGGCCC
CGGAGAGACTCTGTGCGGAGGGGAGCTTGTTGACACGCTTCAGTTTGTC
TGTTCGGACCGCGGCTTCTACTTCAGCAGGCCTTCAAGCCGTGCCAACC
GTCGCAGCCGTGGCATCGTGGAAGAGTGCTGCTTCCGCAGCTGCGACCT
GGCCCTCCTGGAGACATACTGTGCCACCCCCGCCAAGTCCGAGAGGGAC
GTGTCTACCTCTCAGGCCGTACTTCCGGACGACTTCCCCAGATACCCCG
TGGGCAAGTTCTTCCAATATGACACCTGGAGACAGTCCGCGGGACGCCT
GCGCAGAGGCCTGCCTGCCCTCCTGCGTGCCCGCCGGGGTCGCATGCTT
GCCAAAGAGCTCAAAGAGTTCAGAGAGGCCAAACGTCATCGTCCCCTGA
TCGTGTTACCACCCAAAGACCCCGCCCACGGGGGAGCCTCTTCGGAGAT
GTCCAGCAACCATCAGTGAAGATCTACGGGTGGCATCCCTGTGACCCCT
CCCCAGTGCCTCTCCTGGCCCTGGAAGTTGCCACTCCAGTGCCCACCAG
CCTTGTCCTAATAAAATTAAGTTGCATCATTTTGTCTGACTAGGTGTCC
TTCTATAATATTATGGGGTGGAGGGGGGTGGTATGGAGCAAGGGGCAAG
TTGGGAAGACAACCTGTAGGGCCTGCGGGGTCTATTGGGAACCAAGCTG
GAGTGCAGTGGCACAATCTTGGCTCACTGCAATCTCCGCCTCCTGGGTT
CAAGCGATTCTCCTGCCTCAGCCTCCCGAGTTGTTGGGATTCCAGGCAT
GCATGACCAGGCTCAGCTAATTTTTGTTTTTTTGGTAGAGACGGGGTTT
CACCATATTGGCCAGGCTGGTCTCCAACTCCTAATCTCAGGTGATCTAC
CCACCTTGGCCTCCCAAATTGCTGGGATTACAGGCGTGAACCACTGCTC
CCTTCCCTGTCCTTCTGATTTTGTAGGTAACCACGTGCGGACCGAGCGG
CCGCAGGAACCCCTAGTGATGGAGTTGGCCACTCCCTCTCTGCGCGCTT
GCTCGCTCACTGAGGCCGGGCGACCAAAGGTCCCCGACGCCCGGGGCTT
TGCCCGGGCGGCCTCAGTGAGCGAGCGAGCGCGCAGCTGCCTGCAGGGG
CGCCTGATGCGGTATTTTCTCCTTACGCATCTGTGCGGTATTTCACACC
GCATACGTCAAAGCAACCATAGTACGCGCCCTGTAGCGGCGCATTAAGC
GCGGCGGGTGTGGTGGTTACGCGCAGCGTGACCGCTACACTTGCCAGCG
CCCTAGCGCCCGCTCCTTTCGCTTTCTTCCCTTCCTTTCTCGCCACGTT

TABLE II-continued pAAV2-IGF2 vector sequence

```
CGCCGGCTTTCCCCGTCAAGCTCTAAATCGGGGGCTCCCTTTAGGGTTC
CGATTTAGTGCTTTACGGCACCTCGACCCCAAAAAACTTGATTTGGGTG
ATGGTTCACGTAGTGGGCCATCGCCCTGATAGACGGTTTTTCGCCCTTT
GACGTTGGAGTCCACGTTCTTTAATAGTGGACTCTTGTTCCAAACTGGA
ACAACACTCAACCCTATCTCGGGCTATTCTTTTGATTTATAAGGGATTT
TGCCGATTTCGGCCTATTGGTTAAAAAATGAGCTGATTTAACAAAAATT
TAACGCGAATTTTAACAAAATATTAACGTTTACAATTTTATGGTGCAAT
CTCAGTACAATCTGCTCTGATGCCGCATAGTTAAGCCAGCCCCGACACC
CGCCAACACCCGCTGACGCGCCCTGACGGGCTTGTCTGCTCCCGGCATC
CGCTTACAGACAAGCTGTGACCGTCTCCGGGAGCTGCATGTGTCAGAGG
TTTTCACCGTCATCACCGAAACGCGCGAGACGAAAGGGCCTCGTGATAC
GCCTATTTTTATAGGTTAATGTCATGATAATAATGGTTTCTTAGACGTC
AGGTGGCACTTTTCGGGGAAATGTGCGCGGAACCCCTATTTGTTTATTT
TTCTAAATACATTCAAATATGTATCCGCTCATGAGACAATAACCCTGAT
AAATGCTTCAATAATATTGAAAAAGGAAGAGTATGAGTATTCAACATTT
CCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGG
GTGCACGAGTGGGTTACATCGAACTGGATCTCAACAGCGGTAAGATCCT
TGAGAGTTTTCGCCCCGAAGAACGTTTTCCAATGATGAGCACTTTTAAA
GTTCTGCTATGTGGCGCGGTATTATCCCGTATTGACGCCGGGCAAGAGC
AACTCGGTCGCCGCATACACTATTCTCAGAATGACTTGGTTGAGTACTC
ACCAGTCACAGAAAAGCATCTTACGGATGGCATGACAGTAAGAGAATTA
TGCAGTGCTGCCATAACCATGAGTGATAACACTGCGGCCAACTTACTTC
TGACAACGATCGGAGGACCGAAGGAGCTAACCGCTTTTTTGCACAACAT
GGGGGATCATGTAACTCGCCTTGATCGTTGGGAACCGGAGCTGAATGAA
GCCATACCAAACGACGAGCGTGACACCACGATGCCTGTAGCAATGGCAA
CAACGTTGCGCAAACTATTAACTGGCGAACTACTTACTCTAGCTTCCCG
GCAACAATTAATAGACTGGATGGAGGCGGATAAAGTTGCAGGACCACTT
CTGCGCTCGGCCCTTCCGGCTGGCTGGTTTATTGCTGATAAATCTGGAG
CCGGTGAGCGTGGGTCTCGCGGTATCATTGCAGCACTGGGGCCAGATGG
TAAGCCCTCCCGTATCGTAGTTATCTACACGACGGGGAGTCAGGCAACT
ATGGATGAACGAAATAGACAGATCGCTGAGATAGGTGCCTCACTGATTA
AGCATTGGTAACTGTCAGACCAAGTTTACTCATATATACTTTAGATTGA
TTTAAAACTTCATTTTTAATTTAAAAGGATCTAGGTGAAGATCCTTTTT
GATAATCTCATGACCAAAATCCCTTAACGTGAGTTTTCGTTCCACTGAG
CGTCAGACCCCGTAGAAAAGATCAAAGGATCTTCTTGAGATCCTTTTTT
TCTGCGCGTAATCTGCTGCTTGCAAACAAAAAAACCACCGCTACCAGCG
GTGGTTTGTTTGCCGGATCAAGAGCTACCAACTCTTTTTCCGAAGGTAA
CTGGCTTCAGCAGAGCGCAGATACCAAATACTGTCCTTCTAGTGTAGCC
GTAGTTAGGCCACCACTTCAAGAACTCTGTAGCACCGCCTACATACCTC
GCTCTGCTAATCCTGTTACCAGTGGCTGCTGCCAGTGGCGATAAGTCGT
GTCTTACCGGGTTGGACTCAAGACGATAGTTACCGGATAAGGCGCAGCG
GTCGGGCTGAACGGGGGGTTCGTGCACACAGCCCAGCTTGGAGCGAACG
ACCTACACCGAACTGAGATACCTACACGGTGAGCTATGAGAAAGCGCCA
CGCTTCCCGAAGGGAGAAAGGCGGACAGGTATCCGGTAAGCGGCAGGGT
CGGAACAGGAGAGCGCACGAGGGAGCTTCCAGGGGGAAACGCCTGGTAT
CTTTTATAGTCCTGTCGGGTTTCGCCACCTCTGACTTGAGCGTCGATTTT
TGTGATGCTCGTCAGGGGGGCGGAGCCTATGGAAAAACGCCAGCAACGC
GGCCTTTTTACGGTTCCTGGCCTTTTGCTGGCCTTTTGCTCACATGT
```

Characteristics:
    IGF2: [1339: 1878-CW]
    F1 origin: [3066: 2626-CW]
    Stop: [1339: 1878-CW]
    L-ITR: [2430: 2528-CW]
    R-ITR: [12: 106-CW]
    M13 origin: [2621: 3076-CW]
    ColE1 origin: [4472: 5100-CW]
    AmpR: [3661: 4320-CW]
    Amp Prom: [3393: 3421-CW]
    hGH polyA signal: [1889: 2369-CW]
    CMV immediate-early promoter: [170: 721-CW]
    Internal b Glob and CAG enhancer: [820: 1312-CW]

TABLE III

AAV2-IGF2 HA vector sequence

```
CCTGCAGGCAGCTGCGCGCTCGCTCGCTCACTGAGGCCGCCCGGGCAAA
GCCCGGGCGTCGGGCGACCTTTGGTCGCCCGGCCTCAGTGAGCGAGCGA
GCGCGCAGAGAGGGAGTGGCCAACTCCATCACTAGGGGTTCCTGCGGCC
GCACGCGTGGAGCTAGTTATTAATAGTAATCAATTACGGGGTCATTAGT
TCATAGCCCATATATGGAGTTCCGCGTTACATAACTTACGGTAAATGGC
```

TABLE III-continued

AAV2-IGF2 HA vector sequence

```
5    CCGCCTGGCTGACCGCCCAACGACCCCCGCCCATTGACGTCAATAATGA
     CGTATGTTCCCATAGTAACGTCAATAGGGACTTTCCATTGACGTCAATG
     GGTGGAGTATTTACGGTAAACTGCCCACTTGGCAGTACATCAAGTGTAT
     CATATGCCAAGTACGCCCCCTATTGACGTCAATGACGGTAAATGGCCCG
     CCTGGCATTATGCCCAGTACATGACCTTATGGGACTTTCCTACTTGGCA
     GTACATCTACGTATTAGTCATCGCTATTACCATGGTGATGCGGTTTTGG
     CAGTACATCAATGGGCGTGGATAGCGGTTTGACTCACGGGGATTTCCAA
10   GTCTCCACCCCATTGACGTCAATGGGAGTTTGTTTTGCACCAAAATCAA
     CGGGACTTTCCAAAATGTCGTAACAACTCCGCCCCATTGACGCAAATGG
     GCGGTAGGCGTGTACGGTGGGAGGTCTATATAAGCAGAGCTCGTTTAGT
     GAACCGTCAGATCGCCTGGAGACGCCATCCACGCTGTTTTGACCTCCAT
     AGAAGACACCGGGACCGATCCAGCCTCCGCGGATTCGAATCCCGGCCGG
     GAACGGTGCATTGGAACGCGGATTCCCCGTGCCAAGAGTGACGTAAGTA
15   CCGCCTATAGAGTCTATAGGCCCACAAAAAATGCTTTCTTCTTTTAATA
     TACTTTTTTGTTTATCTTATTTCTAATACTTTCCCTAATCTCTTTCTTT
     CAGGGCAATAATGATACAATGTATCATGCCTCTTTGCACCATTCTAAAG
     AATAACAGTGATAATTTCTGGGTTAAGGCAATAGCAATATTTCTGCATA
     TAAATATTTCTGCATATAAATTGTAACTGATGTAAGAGGTTTCATATTG
     CTAATAGCAGCTACAATCCAGCTACCATTCTGCTTTTATTTTATGGTTG
20   GGATAAGGCTGGATTATTCTGAGTCCAAGCTAGGCCCTTTTGCTAATCA
     TGTTCATACCTCTTATCTTCCTCCCACAGCTCCTGGGCAACGTGCTGGT
     CTGTGTGCTGGCCCATCACTTTGGCAAAGAATTGGGATTCGAACATCGA
     TTGAATTCCCTGGCTATGGGGATCCCAGTGGGGAAGTCGATGTTGGTGC
     TTCTCATCTCTTTGGCCTTCGCCTTGTGCTGCATCGCTGCTTACGGCCC
     CGGAGAGACTCTGTGCGGAGGGGAGCTTGTTGACACGCTTCAGTTTGTC
25   TGTTCGGACCGCGCGCTTCTACTTCAGCAGGCCTTCAAGCCGTGCCAACC
     GTCGCAGCCGTGGCATCGTGGAAGAGTGCTGCTTCCGCAGCTGCGACCT
     GGCCCTCCTGGAGACATACTGTGCCACCCCCGCCAAGTCCGAGAGGGAC
     GTGTCTACCTCTCAGGCCGTACTTCCGGACGACTTCCCCAGATACCCCG
     TGGGCAAGTTCTTCCAATATGACACCTGGAGACAGTCCGCGGGACGCCT
     GCGCAGAGGCCTGCCTGCCCTCCTGCGTGCCCGCCGGGGTCGCATGCTT
30   GCCAAAGAGCTCAAAGAGTTCAGAGAGGCCAAACGTCATCGTCCCCTGA
     TCGTGTTACCACCCAAAGACCCCGCCCACGGGGGAGCCTCTTCGGAGAT
     GTCCAGCAACCATCAGTACCCATACGATGTTCCAGATTACGTCTAAAGA
     TCTACGGGTGGCATCCCTGTGACCCCTCCCCAGTGCCTCTCCTGGCCCT
     GGAAGTTGCCACTCCAGTGCCCACCAGCCTTGTCCTAATAAAATTAAGT
     TGCATCATTTTGTCTGACTAGGTGTCCTTCTATAATATTATGGGGTGGA
     GGGGGGTGGTATGGAGCAAGGGGCAAGTTGGGAAGACAACCTGTAGGGC
35   CTGCGGGGTCTATTGGGAACCAAGCTGGAGTGCAGTGGCACAATCTTGG
     CTCACTGCAATCTCCGCCTCCTGGGTTCAAGCGATTCTCCTGCCTCAGC
     CTCCCGAGTTGTTGGGATTCCAGGCATGCATGACCAGGCTCAGCTAATT
     TTTGTTTTTTTGGTAGAGACGGGGTTTCACCATATTGGCCAGGCTGGTC
     TCCAACTCCTAATCTCAGGTGATCTACCCACCTTGGCCTCCCAAATTGC
     TGGGATTACAGGCGTGAACCACTGCTCCCTTCCCTGTCCTTCTGATTTT
     GTAGGTAACCACGTGCGGACCGAGCGGCCGCAGGAACCCCTAGTGATGG
40   AGTTGGCCACTCCCTCTCTGCGCGCTCGCTCGCTCACTGAGGCCGGGCG
     ACCAAAGGTCGCCCGACGCCCGGGCTTTGCCCGGGCGGCCTCAGTGAGC
     GAGCGAGCGCGCAGCTGCCTGCAGGGGCGCCTGATGCGGTATTTTCTCC
     TTACGCATCTGTGCGGTATTTCACACCGCATACGTCAAAGCAACCATAG
     TACGCGCCCTGTAGCGGCGCATTAAGCGCGGCGGGTGTGGTGGTTACGC
     GCAGCGTGACCGCTACACTTGCCAGCGCCCTAGCGCCCGCTCCTTTCGC
45   TTTCTTCCCTTCCTTTCTCGCCACGTTCGCCGGCTTTCCCCGTCAAGCT
     CTAAATCGGGGGCTCCCTTTAGGGTTCCGATTTAGTGCTTTACGGCACC
     TCGACCCCAAAAAACTTGATTTGGGTGATGGTTCACGTAGTGGGCCATC
     GCCCTGATAGACGGTTTTTCGCCCTTTGACGTTGGAGTCCACGTTCTTT
     AATAGTGGACTCTTGTTCCAAACTGGAACAACACTCAACCCTATCTCGG
     GCTATTCTTTTGATTTATAAGGGATTTTGCCGATTTCGGCCTATTGGTT
50   AAAAAATGAGCTGATTTAACAAAAATTTAACGCGAATTTTAACAAAATA
     TTAACGTTTACAATTTTATGGTGCACTCTCAGTACAATCTGCTCTGATG
     CCGCATAGTTAAGCCAGCCCCGACACCCGCCAACACCCGCTGACGCGCC
     CTGACGGGCTTGTCTGCTCCCGGCATCCGCTTACAGACAAGCTGTGACC
     GTCTCCGGGAGCTGCATGTGTCAGAGGTTTTCACCGTCATCACCGAAAC
     GCGCGAGACGAAAGGGCCTCGTGATACGCCTATTTTTATAGGTTAATGT
55   CATGATAATAATGGTTTCTTAGACGTCAGGTGGCACTTTTCGGGGAAAT
     GTGCGCGGAACCCCTATTTGTTTATTTTTCTAAATACATTCAAATATGT
     ATCCGCTCATGAGACAATAACCCTGATAAATGCTTCAATAATATTGAAA
     AAGGAAGAGTATGAGTATTCAACATTTCCGTGTCGCCCTTATTCCCTTT
     TTTGCGGCATTTTGCCTTCCTGTTTTTGCTCACCCAGAAACGCTGGTGA
     AAGTAAAAGATGCTGAAGATCAGTTGGGTGCACGAGTGGGTTACATCGA
60   ACTGGATCTCAACAGCGGTAAGATCCTTGAGAGTTTTCGCCCCGAAGAA
     CGTTTTCCAATGATGAGCACTTTTAAAGTTCTGCTATGTGGCGCGGTAT
     TATCCCGTATTGACGCCGGGCAAGAGCAACTCGGTCGCCGCATACACTA
     TTCTCAGAATGACTTGGTTGAGTACTCACCAGTCACAGAAAAGCATCTT
     ACGGATGGCATGACAGTAAGAGAATTATGCAGTGCTGCCATAACCATGA
     GTGATAACACTGCGGCCAACTTACTTCTGACAACGATCGGAGGACCGAA
     GGAGCTAACCGCTTTTTTGCACAACATGGGGGATCATGTAACTCGCCTT
65   GATCGTTGGGAACCGGAGCTGAATGAAGCCATACCAAACGACGAGCGTG
     ACACCACGATGCCTGTAGCAATGGCAACAACGTTGCGCAAACTATTAAC
```

TABLE III-continued

AAV2-IGF2 HA vector sequence

```
TGGCGAACTACTTACTCTAGCTTCCCGGCAACAATTAATAGACTGGATG
GAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGG
TATCATTGCAGCACTGGGGCCAGATGGTAAGCCCTCCCGTATCGTAGTT
ATCTACACGACGGGGAGTCAGGCAACTATGGATGAACGAAATAGACAGA
TCGCTGAGATAGGTGCCTCACTGATTAAGCATTGGTAACTGTCAGACCA
AGTTTACTCATATATACTTTAGATTGATTTAAAACTTCATTTTTAATTT
AAAAGGATCTAGGTGAAGATCCTTTTTGATAATCTCATGACCAAAATCC
CTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTG
CAAACAAAAAAACCACCGCTACCAGCGGTGGTTTGTTTGCCGGATCAAG
AGCTACCAACTCTTTTTCCGAAGGTAACTGGCTTCAGCAGAGCGCAGAT
ACCAAATACTGTCCTTCTAGTGTAGCCGTAGTTAGGCCACCACTTCAAG
AACTCTGTAGCACCGCCTACATACCTCGCTCTGCTAATCCTGTTACCAG
TGGCTGCTGCCAGTGGCGATAAGTCGTGTCTTACCGGGTTGGACTCAAG
ACGATAGTTACCGGATAAGGCGCAGCGGTCGGGCTGAACGGGGGGGTTCG
TGCACACAGCCCAGCTTGGAGCGAACGACCTACACCGAACTGAGATACC
TACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTC
GCCACCTCTGACTTGAGCGTCGATTTTTGTGATGCTCGTCAGGGGGGCG
GAGCCTATGGAAAAACGCCAGCAACGCGGCCTTTTTACGGTTCCTGGCC
TTTTGCTGGCCTTTTGCTCACATGT
```

Characteristics:
IGF2: [1339: 1878-CW]
F1 origin: [3093: 2653-CW]
HA: [1879: 1908-CW]
L-ITR: [89: 196-CW]
R-ITR: [12: 106-CW]
T7: [2587: 2606-CW]
T7: [3532: 3551-CW]
M13 origin: [2648: 3103-CW]
ColE1 origin: [4499: 5127-CW]
AmpR: [3688: 4347-CW]
Amp Prom: [3420: 3448-CW]
hGH polyA signal: [1916: 2396-CW]
CMV immediate-early promoter: [170: 721-CW]
Internal b Glob y CAG enhancer: [820: 1312-CW]

TABLE IV

Igf2 (Murine)

```
TGGGGATCCCAGTGGGGAAGTCGATGTTGGTGCTTCTCATCTCTTTGGCC
TTCGCCTTGTGCTGCATCGCTGCTTACGGCCCCGGAGAGACTCTGTGCGG
```

TABLE IV-continued

Igf2 (Murine)

```
AGGGGAGCTTGTTGACACGCTTCAGTTTGTCTGTTCGGACCGCGGCTTCT
ACTTCAGCAGGCCTTCAAGCCGTGCCAACCGTCGCAGCCGTGGCATCGTG
GAAGAGTGCTGCTTCCGCAGCTGCGACCTGGCCCTCCTGGAGACATACTG
TGCCACCCCCGCCAAGTCCGAGAGGGACGTGTCTACCTCTCAGGCCGTAC
TTCCGGACGACTTCCCCAGATACCCCGTGGGCAAGTTCTTCCAATATGAC
ACCTGGAGACAGTCCGCGGGACGCCTGCGCAGAGGCCTGCCTGCCCTCCT
GCGTGCCCGCCGGGGTCGCATGCTTGCCAAAGAGCTCAAAGAGTTCAGAG
AGGCCAAACGTCATCGTCCCCTGATCGTGTTACCACCCAAAGACCCCGCC
CACGGGGGAGCCTCTTCGGAGATGTCCAGCAACCATCAG
```

TABLE V

Igf2-HA (Murine)

```
TGGGGATCCCAGTGGGGAAGTCGATGTTGGTGCTTCTCATCTCTTTGGCC
TTCGCCTTGTGCTGCATCGCTGCTTACGGCCCCGGAGAGACTCTGTGCGG
AGGGGAGCTTGTTGACACGCTTCAGTTTGTCTGTTCGGACCGCGGCTTCT
ACTTCAGCAGGCCTTCAAGCCGTGCCAACCGTCGCAGCCGTGGCATCGTG
GAAGAGTGCTGCTTCCGCAGCTGCGACCTGGCCCTCCTGGAGACATACTG
TGCCACCCCCGCCAAGTCCGAGAGGGACGTGTCTACCTCTCAGGCCGTAC
TTCCGGACGACTTCCCCAGATACCCCGTGGGCAAGTTCTTCCAATATGAC
ACCTGGAGACAGTCCGCGGGACGCCTGCGCAGAGGCCTGCCTGCCCTCCT
GCGTGCCCGCCGGGGTCGCATGCTTGCCAAAGAGCTCAAAGAGTTCAGAG
AGGCCAAACGTCATCGTCCCCTGATCGTGTTACCACCCAAAGACCCCGCC
CACGGGGGAGCCTCTTCGGAGATGTCCAGCAACCATCAGTACCCATACGA
TGTTCCAGATTACGTCTAA
```

TABLE VII

IGF2 (Human)

```
ATGGGAATCCCAATGGGGAAGTCGATGCTGGTGCTTCTCACCTTCTTGGC
CTTCGCCTCGTGCTGCATTGCTGCTTACCGCCCCAGTGAGACCCTGTGCG
GCGGGGAGCTGGTGGACACCCTCCAGTTCGTCTGTGGGGACCGCGGCTTC
TACTTCAGCAGGCCCGCAAGCCGTGTGAGCCGTCGCAGCCGTGGCATCGT
TGAGGAGTGCTGTTTCCGCAGCTGTGACCTGGCCCTCCTGGAGACGTACT
GTGCTACCCCCGCCAAGTCCGAGAGGGACGTGTCGACCCCTCCGACCGTG
CTTCCGGACAACTTCCCCAGATACCCCGTGGGCAAGTTCTTCCAATATGA
CACCTGGAAGCAGTCCACCCAGCGCCTGCGCAGGGGCCTGCCTGCCCTCC
TGCGTGCCCGCCGGGGTCACGTGCTCGCCAAGGAGCTCGAGGCGTTCAGG
GAGGCCAAACGTCACCGTCCCCTGATTGCTCTACCCACCCAAGACCCCGC
CCACGGGGGCGCCCCCCAGAGATGGCCAGCAATCGGAAGTGA
```

The invention claimed is:

1. A therapeutic method for treatment of Huntington's disease in a subject in need thereof, the method comprising:

administering a therapeutically effective amount of a pharmaceutical composition to said subject directly to striatum in brain by stereotactic intrastriatal injection, wherein said pharmaceutical composition comprises:

an adeno-associated virus (AAV), serotype AAV2, comprising a recombinant viral genome, wherein said genome comprises an expression cassette comprising a CAG promoter operably linked to a polynucleotide of interest that encodes for human IGF2; and a pharmaceutically acceptable excipient.

2. The therapeutic method of treatment according to claim 1, wherein the composition is injected unilateral or bilaterally.

3. A plasmid, comprising sequences of an adeno-associated vector, and an expression cassette flanked by ITRs of an adeno-associated virus, wherein said expression cassette comprises a promoter, and a polynucleotide of interest that encodes IGF2, wherein the plasmid is one of those deposited at an international agent of biological deposit, Chilean Collection of Microbial Genetic Resources (CChRGM), having deposit numbers RGM2335 and RGM2336.

4. The therapeutic method of treatment according to claim 1, wherein the pharmaceutical composition induces an overexpression of IGF2 that reduces aggregation of mutant huntingtin (mHtt) in neuronal cells in said subject.

5. The therapeutic method of treatment according to claim 1, wherein said subject is a human.

6. A pharmaceutical composition for treatment of Huntington's disease in a subject in need thereof, the pharmaceutical composition comprising:

an adeno-associated virus (AAV), serotype AAV2, comprising a recombinant viral genome, wherein said genome comprises an expression cassette comprising a CAG promoter operably linked to a polynucleotide of interest that encodes for human IGF2, wherein said expression cassette is included in one of those plasmid deposited at international agent of biological deposit, Chilean Collection of Microbial Genetic Resources (CChRGM), having deposit numbers RGM2335 and RGM2336; and a pharmaceutically acceptable excipient, wherein the composition is formulated to be administered directly to brain of said subject.

7. A therapeutic method for treatment of Huntington's disease in a subject in need thereof, the method comprising:

administering a therapeutically effective amount of the pharmaceutical composition of claim 6 to said subject directly to striatum in the brain by stereotactic intrastriatal injection.

8. The therapeutic method of treatment according to claim 7, wherein the composition is injected unilateral or bilaterally.

9. The therapeutic method of treatment according to claim 7, wherein the pharmaceutical composition induces an overexpression of IGF2 that reduces aggregation of mutant huntingtin (mHtt) in neuronal cells in said subject.

* * * * *

SEQUENCE LISTING

<160> NUMBER OF SEQ ID NOS: 15

<210> SEQ ID NO 1
<211> LENGTH: 4679
<212> TYPE: DNA
<213> ORGANISM: adeno-associated virus 2
<300> PUBLICATION INFORMATION:
<308> DATABASE ACCESSION NUMBER: GenBank AF043303.1
<309> DATABASE ENTRY DATE: 2010-05-20
<313> RELEVANT RESIDUES IN SEQ ID NO: (1)..(4679)

<400> SEQUENCE: 1

```
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcctggagg ggtggagtcg tgacgtgaat tacgtcatag       180
ggttagggag gtcctgtatt agaggtcacg tgagtgtttt gcgacatttt gcgacaccat       240
```

```
gtggtcacgc tgggtattta agcccgagtg agcacgcagg gtctccattt tgaagcggga      300
ggtttgaacg cgcagccgcc atgccggggt tttacgagat tgtgattaag gtccccagcg      360
accttgacga gcatctgccc ggcatttctg acagctttgt gaactgggtg gccgagaagg      420
aatgggagtt gccgccagat tctgacatgg atctgaatct gattgagcag gcacccctga      480
ccgtggccga gaagctgcag cgcgactttc tgacggaatg gcgccgtgtg agtaaggccc      540
cggaggccct tttctttgtg caatttgaga agggagagag ctacttccac atgcacgtgc      600
tcgtggaaac caccggggtg aaatccatgg tttttgggacg tttcctgagt cagattcgcg      660
aaaaactgat tcagagaatt taccgcggga tcgagccgac tttgccaaac tggttcgcgg      720
tcacaaagac cagaaatggc gccggaggcg ggaacaaggt ggtggatgag tgctacatcc      780
ccaattactt gctccccaaa acccagcctg agctccagtg ggcgtggact aatatggaac      840
agtatttaag cgcctgtttg aatctcacgg agcgtaaacg gttggtggcg cagcatctga      900
cgcacgtgtc gcagacgcag gagcagaaca aagagaatca gaatcccaat tctgatgcgc      960
cggtgatcag atcaaaaact tcagccaggt acatggagct ggtcgggtgg ctcgtggaca     1020
aggggattac ctcggagaag cagtggatcc aggaggacca ggcctcatac atctccttca     1080
atgcggcctc caactcgcgg tcccaaatca aggctgcctt ggacaatgcg ggaaagatta     1140
tgagcctgac taaaaccgcc cccgactacc tggtgggcca gcagcccgtg gaggacattt     1200
ccagcaatcg gatttataaa attttggaac taaacgggta cgatccccaa tatgcggctt     1260
ccgtctttct gggatgggcc acgaaaaagt tcggcaagag gaacaccatc tggctgtttg     1320
ggcctgcaac taccgggaag accaacatcg cggaggccat agcccacact gtgcccttct     1380
acgggtgcgt aaactggacc aatgagaact ttcccttcaa cgactgtgtc gacaagatgg     1440
tgatctggtg ggaggagggg aagatgaccg ccaaggtcgt ggagtcggcc aaagccattc     1500
tcggaggaag caaggtgcgc gtggaccaga aatgcaagtc ctcggcccag atagacccga     1560
ctcccgtgat cgtcacctcc aacaccaaca tgtgcgccgt gattgacggg aactcaacga     1620
ccttcgaaca ccagcagccg ttgcaagacc ggatgttcaa atttgaactc acccgccgtc     1680
tggatcatga ctttgggaag gtcaccaagc aggaagtcaa agactttttc cggtgggcaa     1740
aggatcacgt ggttgaggtg gagcatgaat tctacgtcaa aaagggtgga gccaagaaaa     1800
gacccgcccc cagtgacgca gatataagtg agcccaaacg ggtgcgcgag tcagttgcgc     1860
agccatcgac gtcagacgcg gaagcttcga tcaactacgc agacaggtac caaaacaaat     1920
gttctcgtca cgtgggcatg aatctgatgc tgtttccctg cagacaatgc gagagaatga     1980
atcagaattc aaatatctgc ttcactcacg gacagaaaga ctgtttagag tgctttcccg     2040
tgtcagaatc tcaacccgtt tctgtcgtca aaaaggcgta tcagaaactg tgctacattc     2100
atcatatcat gggaaaggtg ccagacgctt gcactgcctg cgatctggtc aatgtggatt     2160
tggatgactg catctttgaa caataaatga tttaaatcag gtatggctgc cgatggttat     2220
cttccagatt ggctcgagga cactctctct gaaggaataa gacagtggtg gaagctcaaa     2280
cctggcccac caccaccaaa gcccgcagag cggcataagg acgacagcag gggtcttgtg     2340
cttcctgggt acaagtacct cggacccttc aacggactcg acaagggaga gccggtcaac     2400
gaggcagacg ccgcggccct cgagcacgac aaagcctacg accggcagct cgacagcgga     2460
gacaacccgt acctcaagta caaccacgcc gacgcggagt tcaggagcg ccttaaagaa     2520 gatacgtctt ttgggggcaa cctcggacga gcagtcttcc aggcgaaaaa gagggttctt     2580
```

```
gaacctctgg gcctggttga ggaacctgtt aagacggctc cgggaaaaaa gaggccggta     2640
gagcactctc ctgtggagcc agactcctcc tcgggaaccg gaaaggcggg ccagcagcct     2700
gcaagaaaaa gattgaattt tggtcagact ggagacgcag actcagtacc tgaccccag     2760 cctctcggac agccaccagc agccccctct ggtctgggaa ctaatacgat ggctacaggc     2820
agtggcgcac caatggcaga caataacgag ggcgccgacg gagtgggtaa ttcctcggga     2880
aattggcatt gcgattccac atggatgggc gacagagtca tcaccaccag cacccgaacc     2940
tgggccctgc ccacctacaa caaccacctc tacaaacaaa tttccagcca atcaggagcc     3000
tcgaacgaca tcactactt tggctacagc accccttggg ggtattttga cttcaacaga     3060
ttccactgcc acttttcacc acgtgactgg caaagactca tcaacaacaa ctggggattc     3120
cgacccaaga gactcaactt caagctcttt aacattcaag tcaaagaggt cacgcagaat     3180
gacggtacga cgacgattgc caataacctt accagcacgg ttcaggtgtt tactgactcg     3240
gagtaccagc tcccgtacgt cctcggctcg gcgcatcaag gatgcctccc gccgttccca     3300
gcagacgtct tcatggtgcc acagtatgga tacctcaccc tgaacaacgg gagtcaggca     3360
gtaggacgct cttcatttta ctgcctggag tactttcctt ctcagatgct gcgtaccgga     3420
aacaacttta ccttcagcta cacttttgag gacgttcctt ccacagcag ctacgctcac      3480 agccagagtc tggaccgtct catgaatcct ctcatcgacc agtacctgta ttacttgagc     3540
agaacaaaca ctccaagtgg aaccaccacg cagtcaaggc ttcagttttc tcaggccgga     3600
gcgagtgaca ttcgggacca gtctaggaac tggcttcctg gaccctgtta ccgccagcag     3660
cgagtatcaa agacatctgc ggataacaac aacagtgaat actcgtggac tggagctacc     3720
aagtaccacc tcaatggcag agactctctg gtgaatccgg gcccggccat ggcaagccac     3780
aaggacgatg aagaaaagtt ttttcctcag agcgggggttc tcatctttgg gaagcaaggc     3840
tcagagaaaa caaatgtgga cattgaaaag gtcatgatta cagacgaaga ggaaatcagg     3900
acaaccaatc ccgtggctac ggagcagtat ggttctgtat ctaccaacct ccagagaggc     3960
aacagacaag cagctaccgc agatgtcaac acacaaggcg ttcttccagg catggtctgg     4020
caggacagag atgtgtacct tcaggggccc atctgggcaa agattccaca cacggacgga     4080
cattttcacc cctctcccct catgggtgga ttcggactta aacaccctcc tccacagatt     4140
ctcatcaaga acacccggt acctgcgaat ccttcgacca ccttcagtgc ggcaaagttt      4200
gcttccttca tcacacagta ctccacggga caggtcagcg tggagatcga gtgggagctg     4260
cagaaggaaa acagcaaacg ctggaatccc gaaattcagt acacttccaa ctacaacaag     4320
tctgttaatg tggactttac tgtggacact aatggcgtgt attcagagcc tcgccccatt     4380
ggcaccagat acctgactcg taatctgtaa ttgcttgtta atcaataaac cgtttaattc     4440
gtttcagttg aactttggtc tctgcgtatt tctttcttat ctagtttcca tggctacgta     4500
gataagtagc atggcgggtt aatcattaac tacaaggaac ccctagtgat ggagttggcc     4560
actccctctc tgcgcgctcg ctcgctcact gaggccgggc gaccaaaggt cgcccgacgc     4620
ccgggctttg cccgggcggc ctcagtgagc gagcgagcgc gcagagaggg agtggccaa      4679
```

<210> SEQ ID NO 2
<211> LENGTH: 5143
<212> TYPE: DNA
<213> ORGANISM: Artificial Sequence
<220> FEATURE:
<223> OTHER INFORMATION: Plasmid pAAV2-IGF2
<220> FEATURE:
<221> NAME/KEY: R-ITR

```
<222> LOCATION: (12)..(106)
<220> FEATURE:
<221> NAME/KEY: CMV_immearly_promoter
<222> LOCATION: (170)..(721)
<220> FEATURE:
<221> NAME/KEY: bGlob_int
<222> LOCATION: (820)..(1312)
<220> FEATURE:
<221> NAME/KEY: CAG_enhancer
<222> LOCATION: (820)..(1312)
<220> FEATURE:
<221> NAME/KEY: IGF2
<222> LOCATION: (1339)..(1878)
<220> FEATURE:
<221> NAME/KEY: Stop
<222> LOCATION: (1339)..(1878)
<220> FEATURE:
<221> NAME/KEY: hGH_polyA_signal
<222> LOCATION: (1889)..(2369)
<220> FEATURE:
<221> NAME/KEY: L-ITR
<222> LOCATION: (2430)..(2528)
<220> FEATURE:
<221> NAME/KEY: M13_origin
<222> LOCATION: (2621)..(3076)
<220> FEATURE:
<221> NAME/KEY: F1 origin
<222> LOCATION: (2626)..(3066)
<220> FEATURE:
<221> NAME/KEY: AmpR_Prom
<222> LOCATION: (3393)..(3421)
<220> FEATURE:
<221> NAME/KEY: AmpR
<222> LOCATION: (3661)..(4320)
<220> FEATURE:
<221> NAME/KEY: ColE1_origin
<222> LOCATION: (4472)..(5100)

<400> SEQUENCE: 2
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtggagc tagttattaa tagtaatcaa     180
ttacggggtc attagttcat agcccatata tggagttccg cgttacataa cttacggtaa     240
atggcccgcc tggctgaccg cccaacgacc cccgcccatt gacgtcaata atgacgtatg     300
ttcccatagt aacgtcaata gggactttcc attgacgtca atgggtggag tatttacggt     360
aaactgccca cttggcagta catcaagtgt atcatatgcc aagtacgccc cctattgacg     420
tcaatgacgg taaatggccc gcctggcatt atgcccagta catgacctta tgggactttc     480
ctacttggca gtacatctac gtattagtca tcgctattac catggtgatg cggttttggc     540
agtacatcaa tgggcgtgga tagcggtttg actcacgggg atttccaagt ctccacccca     600
ttgacgtcaa tgggagtttg ttttgcacca aaatcaacgg gactttccaa aatgtcgtaa     660
caactccgcc ccattgacgc aaatgggcgg taggcgtgta cggtgggagg tctatataag     720
cagagctcgt ttagtgaacc gtcagatcgc ctggagacgc catccacgct gttttgacct     780
ccatagaaga caccgggacc gatccagcct ccgcggattc gaatcccggc cgggaacggt     840
gcattggaac gcggattccc cgtgccaaga gtgacgtaag taccgcctat agagtctata     900
ggcccacaaa aaatgctttc ttcttttaat atactttttt gtttatctta tttctaatac     960
tttccctaat ctctttcttt cagggcaata atgatacaat gtatcatgcc tctttgcacc    1020
attctaaaga ataacagtga taatttctgg gttaaggcaa tagcaatatt tctgcatata    1080
aatatttctg catataaatt gtaactgatg taagaggttt catattgcta atagcagcta    1140
caatccagct accattctgc ttttatttta tggttgggat aaggctggat tattctgagt    1200
```

```
ccaagctagg ccctttttgct aatcatgttc atacctctta tcttcctccc acagctcctg   1260
ggcaacgtgc tggtctgtgt gctggcccat cactttggca aagaattggg attcgaacat   1320
cgattgaatt ccctggctat ggggatccca gtggggaagt cgatgttggt gcttctcatc   1380
tctttggcct tcgccttgtg ctgcatcgct gcttacggcc ccggagagac tctgtgcgga   1440
ggggagcttg ttgacacgct tcagtttgtc tgttcggacc gcggcttcta cttcagcagg   1500
ccttcaagcc gtgccaaccg tcgcagccgt ggcatcgtgg aagagtgctg cttccgcagc   1560
tgcgacctgg ccctcctgga gacatactgt gccacccccg ccaagtccga gagggacgtg   1620
tctacctctc aggccgtact tccggacgac ttccccagat accccgtggg caagttcttc   1680
caatatgaca cctggagaca gtccgcggga cgcctgcgca gaggcctgcc tgccctcctg   1740
cgtgcccgcc ggggtcgcat gcttgccaaa gagctcaaag agttcagaga ggccaaacgt   1800
catcgtcccc tgatcgtgtt accacccaaa gaccccgccc acgggggagc ctcttcggag   1860
atgtccagca accatcagtg aagatctacg ggtggcatcc ctgtgacccc tccccagtgc   1920
ctctcctggc cctggaagtt gccactccag tgcccaccag ccttgtccta ataaaattaa   1980
gttgcatcat tttgtctgac taggtgtcct tctataatat tatggggtgg aggggggtgg   2040
tatggagcaa ggggcaagtt gggaagacaa cctgtagggc ctgcggggtc tattgggaac   2100
caagctggag tgcagtggca caatcttggc tcactgcaat ctccgcctcc tgggttcaag   2160
cgattctcct gcctcagcct cccgagttgt tgggattcca ggcatgcatg accaggctca   2220 gctaatttttt gttttttttgg tagagacggg gtttcaccat attggccagg ctggtctcca   2280
actcctaatc tcaggtgatc tacccacctt ggcctcccaa attgctggga ttacaggcgt   2340
gaaccactgc tcccttccct gtccttctga ttttgtaggt aaccacgtgc ggaccgagcg   2400
gccgcaggaa cccctagtga tggagttggc cactccctct ctgcgcgctc gctcgctcac   2460
tgaggccggg cgaccaaagg tcgcccgacg cccgggcttt gcccgggcgg cctcagtgag   2520
cgagcgagcg cgcagctgcc tgcaggggcg cctgatgcgg tatttttctcc ttacgcatct   2580 gtgcggtatt tcacaccgca tacgtcaaag caaccatagt acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcgggggct cccttttaggg ttccgattta gtgctttacg gcacctcgac   2820
cccaaaaaac ttgatttggg tgatggttca cgtagtgggc catcgccctg atagacggtt   2880
tttcgccctt tgacgttgga gtccacgttc tttaatagtg gactcttgtt ccaaactgga   2940
acaacactca accctatctc gggctattct tttgatttat aagggatttt gccgatttcg   3000
gcctattggt taaaaaatga gctgatttaa caaaaattta acgcgaattt aacaaaata   3060 ttaacgttta caattttatg gtgcactctc agtacaatct gctctgatgc cgcatagtta   3120
agccagcccc gacacccgcc aacacccgct gacgcgccct gacgggcttg tctgctcccg   3180
gcatccgctt acagacaagc tgtgaccgtc tccgggagct gcatgtgtca gaggttttca   3240
ccgtcatcac cgaaacgcgc gagacgaaag ggcctcgtga tacgcctatt tttataggtt   3300
aatgtcatga taataatggt ttcttagacg tcaggtggca ctttttcgggg aaatgtgcgc   3360 ggaaccccta tttgtttatt tttctaaata cattcaaata tgtatccgct catgagacaa   3420
taaccctgat aaatgcttca ataatattga aaaaggaaga gtatgagtat tcaacatttc   3480
cgtgtcgccc ttattccctt ttttgcggca ttttgccttc ctgttttttgc tcacccagaa   3540
```

```
acgctggtga aagtaaaaga tgctgaagat cagttgggtg cacgagtggg ttacatcgaa    3600
ctggatctca acagcggtaa gatccttgag agttttcgcc ccgaagaacg ttttccaatg    3660
atgagcactt ttaaagttct gctatgtggc gcggtattat cccgtattga cgccgggcaa    3720
gagcaactcg gtcgccgcat acactattct cagaatgact tggttgagta ctcaccagtc    3780
acagaaaagc atcttacgga tggcatgaca gtaagagaat tatgcagtgc tgccataacc    3840
atgagtgata acactgcggc caacttactt ctgacaacga tcggaggacc gaaggagcta    3900
accgcttttt tgcacaacat gggggatcat gtaactcgcc ttgatcgttg ggaaccggag    3960
ctgaatgaag ccataccaaa cgacgagcgt gacaccacga tgcctgtagc aatggcaaca    4020
acgttgcgca aactattaac tggcgaacta cttactctag cttcccggca acaattaata    4080
gactggatgg aggcggataa agttgcagga ccacttctgc gctcggccct tccggctggc    4140
tggtttattg ctgataaatc tggagccggt gagcgtgggt ctcgcggtat cattgcagca    4200
ctggggccag atggtaagcc ctcccgtatc gtagttatct acacgacggg gagtcaggca    4260
actatggatg aacgaaatag acagatcgct gagataggtg cctcactgat taagcattgg    4320
taactgtcag accaagttta ctcatatata ctttagattg atttaaaact tcattttttaa   4380 tttaaaagga tctaggtgaa gatccttttt gataatctca tgaccaaaat cccttaacgt    4440
gagttttcgt tccactgagc gtcagacccc gtagaaaaga tcaaaggatc ttcttgagat    4500 ccttttttc tgcgcgtaat ctgctgcttg caaacaaaaa aaccaccgct accagcggtg     4560
gtttgtttgc cggatcaaga gctaccaact ctttttccga aggtaactgg cttcagcaga    4620
gcgcagatac caaatactgt ccttctagtg tagccgtagt taggccacca cttcaagaac    4680
tctgtagcac cgcctacata cctcgctctg ctaatcctgt taccagtggc tgctgccagt    4740
ggcgataagt cgtgtcttac cgggttggac tcaagacgat agttaccgga taaggcgcag    4800
cggtcgggct gaacggggggg ttcgtgcaca gcccagct tggagcgaac gacctacacc     4860
gaactgagat acctacagcg tgagctatga aaagcgcca cgcttcccga agggagaaag     4920
gcggacaggt atccggtaag cggcagggtc ggaacaggag agcgcacgag ggagcttcca    4980
gggggaaacg cctggtatct ttatagtcct gtcgggtttc gccacctctg acttgagcgt    5040
cgatttttgt gatgctcgtc aggggggcgg agcctatgga aaaacgccag caacgcggcc    5100 ttttacggt tcctggcctt ttgctggcct tttgctcaca tgt                       5143
```

<210> SEQ ID NO 3
<211> LENGTH: 5170
<212> TYPE: DNA
<213> ORGANISM: Artificial Sequence
<220> FEATURE:
<223> OTHER INFORMATION: Plasmid pAAV2-IGF2-HA
<220> FEATURE:
<221> NAME/KEY: R-ITR
<222> LOCATION: (12)..(106)
<220> FEATURE:
<221> NAME/KEY: L-ITR
<222> LOCATION: (89)..(196)
<220> FEATURE:
<221> NAME/KEY: CMV_immearly_promoter
<222> LOCATION: (170)..(721)
<220> FEATURE:
<221> NAME/KEY: bGlob_int
<222> LOCATION: (820)..(1312)
<220> FEATURE:
<221> NAME/KEY: CAG_enhancer
<222> LOCATION: (820)..(1312)
<220> FEATURE:
<221> NAME/KEY: IGF2
<222> LOCATION: (1339)..(1878)

```
<220> FEATURE:
<221> NAME/KEY: HA
<222> LOCATION: (1879)..(1908)
<220> FEATURE:
<221> NAME/KEY: hGH_polyA_signal
<222> LOCATION: (1916)..(2396)
<220> FEATURE:
<221> NAME/KEY: T7
<222> LOCATION: (2587)..(2606)
<220> FEATURE:
<221> NAME/KEY: M13_origin
<222> LOCATION: (2648)..(3103)
<220> FEATURE:
<221> NAME/KEY: F1_origin
<222> LOCATION: (2653)..(3093)
<220> FEATURE:
<221> NAME/KEY: AmpR_Prom
<222> LOCATION: (3420)..(3448)
<220> FEATURE:
<221> NAME/KEY: T7
<222> LOCATION: (3532)..(3551)
<220> FEATURE:
<221> NAME/KEY: AmpR
<222> LOCATION: (3688)..(4347)
<220> FEATURE:
<221> NAME/KEY: ColE1_origin
<222> LOCATION: (4499)..(5127)

<400> SEQUENCE: 3
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtggagc tagttattaa tagtaatcaa     180
ttacggggtc attagttcat agcccatata tggagttccg cgttacataa cttacggtaa     240
atggcccgcc tggctgaccg cccaacgacc cccgcccatt gacgtcaata atgacgtatg     300
ttcccatagt aacgtcaata gggactttcc attgacgtca atgggtggag tatttacggt     360
aaactgccca cttggcagta catcaagtgt atcatatgcc aagtacgccc cctattgacg     420
tcaatgacgg taaatggccc gcctggcatt atgcccagta catgacctta tgggactttc     480
ctacttggca gtacatctac gtattagtca tcgctattac catggtgatg cggttttggc     540
agtacatcaa tgggcgtgga tagcggtttg actcacgggg atttccaagt ctccacccca     600
ttgacgtcaa tgggagtttg ttttgcacca aaatcaacgg gactttccaa aatgtcgtaa     660
caactccgcc ccattgacgc aaatgggcgg taggcgtgta cggtgggagg tctatataag     720
cagagctcgt ttagtgaacc gtcagatcgc ctggagacgc catccacgct gttttgacct     780
ccatagaaga caccgggacc gatccagcct ccgcggattc gaatcccggc cgggaacggt     840
gcattggaac gcggattccc cgtgccaaga gtgacgtaag taccgcctat agagtctata     900
ggcccacaaa aaatgctttc ttcttttaat atactttttt gtttatctta tttctaatac     960
tttccctaat ctctttcttt cagggcaata atgatacaat gtatcatgcc tctttgcacc    1020
attctaaaga ataacagtga taatttctgg gttaaggcaa tagcaatatt tctgcatata    1080
aatatttctg catataaatt gtaactgatg taagaggttt catattgcta atagcagcta    1140
caatccagct accattctgc ttttatttta tggttgggat aaggctggat tattctgagt    1200
ccaagctagg cccttttgct aatcatgttc atacctctta tcttcctccc acagctcctg    1260
ggcaacgtgc tggtctgtgt gctggcccat cactttggca aagaattggg attcgaacat    1320
cgattgaatt ccctggctat ggggatccca gtggggaagt cgatgttggt gcttctcatc    1380
tctttggcct tcgccttgtg ctgcatcgct gcttacggcc ccggagagac tctgtgcgga    1440
ggggagcttg ttgacacgct tcagtttgtc tgttcggacc gcggcttcta cttcagcagg    1500
```

-continued

```
ccttcaagcc gtgccaaccg tcgcagccgt ggcatcgtgg aagagtgctg cttccgcagc   1560
tgcgacctgg ccctcctgga gacatactgt gccacccccg ccaagtccga gagggacgtg   1620
tctacctctc aggccgtact tccggacgac ttccccagat accccgtggg caagttcttc   1680
caatatgaca cctggagaca gtccgcggga cgcctgcgca gaggcctgcc tgccctcctg   1740
cgtgcccgcc ggggtcgcat gcttgccaaa gagctcaaag agttcagaga ggccaaacgt   1800
catcgtcccc tgatcgtgtt accacccaaa gaccccgccc acggggagc ctcttcggag    1860 atgtccagca accatcagta cccatacgat gttccagatt acgtctaaag atctacgggt   1920
ggcatccctg tgacccctcc ccagtgcctc tcctggcct ggaagttgcc actccagtgc     1980
ccaccagcct tgtcctaata aaattaagtt gcatcatttt gtctgactag gtgtccttct   2040
ataatattat ggggtggagg ggggtggtat ggagcaaggg gcaagttggg aagacaacct   2100
gtagggcctg cggggtctat tgggaaccaa gctggagtgc agtggcacaa tcttggctca   2160
ctgcaatctc cgcctcctgg gttcaagcga ttctcctgcc tcagcctccc gagttgttgg   2220
gattccaggc atgcatgacc aggctcagct aattttttgtt tttttggtag agacgggtt    2280 tcaccatatt ggccaggctg gtctccaact cctaatctca ggtgatctac ccaccttggc   2340
ctcccaaatt gctgggatta caggcgtgaa ccactgctcc cttccctgtc cttctgattt   2400
tgtaggtaac cacgtgcgga ccgagcggcc gcaggaaccc ctagtgatgg agttggccac   2460
tccctctctg cgcgctcgct cgctcactga ggccgggcga ccaaaggtcg cccgacgccc   2520
gggctttgcc cggcggcct cagtgagcga gcgagcgcgc agctgcctgc aggggcgcct    2580
gatgcggtat tttctcctta cgcatctgtg cggtatttca caccgcatac gtcaaagcaa   2640
ccatagtacg cgccctgtag cggcgcatta agcgcggcgg gtgtggtggt tacgcgcagc   2700
gtgaccgcta cacttgccag cgccctagcg cccgctcctt tcgctttctt cccttccttt   2760
ctcgccacgt tcgccggctt tccccgtcaa gctctaaatc ggggggctccc tttagggttc   2820 cgatttagtg ctttacggca cctcgacccc aaaaaacttg atttgggtga tggttcacgt   2880
agtgggccat cgccctgata gacggttttt cgcccttttga cgttggagtc cacgttcttt   2940
aatagtggac tcttgttcca aactggaaca acactcaacc ctatctcggg ctattctttt   3000
gatttataag ggattttgcc gatttcggcc tattggttaa aaaatgagct gatttaacaa   3060
aaatttaacg cgaatttttaa caaaatatta acgtttacaa ttttatggtg cactctcagt   3120
acaatctgct ctgatgccgc atagttaagc cagccccgac acccgccaac acccgctgac   3180
gcgccctgac gggcttgtct gctcccggca tccgcttaca gacaagctgt gaccgtctcc   3240
gggagctgca tgtgtcagag gttttcaccg tcatcaccga aacgcgcgag acgaaagggc   3300
ctcgtgatac gcctattttt ataggttaat gtcatgataa taatggtttc ttagacgtca   3360
ggtggcactt ttcggggaaa tgtgcgcgga accccttatt gtttattttt ctaaatacat   3420
tcaaatatgt atccgctcat gagacaataa ccctgataaa tgcttcaata atattgaaaa   3480
aggaagagta tgagtattca acatttccgt gtcgccctta ttcccttttt tgcggcattt   3540
tgccttcctg tttttgctca cccagaaacg ctggtgaaag taaaagatgc tgaagatcag   3600
ttgggtgcac gagtgggtta catcgaactg gatctcaaca gcggtaagat ccttgagagt   3660
tttcgccccg aagaacgttt tccaatgatg agcacttta aagttctgct atgtggcgcg    3720
gtattatccc gtattgacgc cgggcaagag caactcggtc gccgcataca ctattctcag   3780
aatgacttgg ttgagtactc accagtcaca gaaaagcatc ttacggatgg catgacagta   3840
```

```
agagaattat gcagtgctgc cataaccatg agtgataaca ctgcggccaa cttacttctg      3900
acaacgatcg gaggaccgaa ggagctaacc gctttttttgc acaacatggg ggatcatgta      3960
actcgccttg atcgttggga accggagctg aatgaagcca taccaaacga cgagcgtgac      4020
accacgatgc ctgtagcaat ggcaacaacg ttgcgcaaac tattaactgg cgaactactt      4080
actctagctt cccggcaaca attaatagac tggatggagg cggataaagt tgcaggacca      4140
cttctgcgct cggcccttcc ggctggctgg tttattgctg ataaatctgg agccggtgag      4200
cgtgggtctc gcggtatcat tgcagcactg gggccagatg gtaagccctc ccgtatcgta      4260
gttatctaca cgacggggag tcaggcaact atggatgaac gaaatagaca gatcgctgag      4320
ataggtgcct cactgattaa gcattggtaa ctgtcagacc aagtttactc atatatactt      4380
tagattgatt taaaacttca ttttttaattt aaaaggatct aggtgaagat ccttttttgat      4440 aatctcatga ccaaaatccc ttaacgtgag ttttcgttcc actgagcgtc agaccccgta      4500
gaaaagatca aaggatcttc ttgagatcct ttttttctgc gcgtaatctg ctgcttgcaa      4560
acaaaaaaac caccgctacc agcggtggtt tgtttgccgg atcaagagct accaactctt      4620
tttccgaagg taactggctt cagcagagcg cagataccaa atactgtcct tctagtgtag      4680
ccgtagttag gccaccactt caagaactct gtagcaccgc ctacatacct cgctctgcta      4740
atcctgttac cagtggctgc tgccagtggc gataagtcgt gtcttaccgg gttggactca      4800
agacgatagt taccggataa ggcgcagcgg tcgggctgaa cggggggttc gtgcacacag      4860
cccagcttgg agcgaacgac ctacaccgaa ctgagatacc tacagcgtga gctatgagaa      4920
agcgccacgc ttcccgaagg gagaaaggcg gacaggtatc cggtaagcgg cagggtcgga      4980
acaggagagc gcacgaggga gcttccaggg ggaaacgcct ggtatcttta tagtcctgtc      5040
gggtttcgcc acctctgact tgagcgtcga ttttttgtgat gctcgtcagg ggggcggagc      5100
ctatggaaaa acgccagcaa cgcggccttt ttacggttcc tggccttttg ctggcctttt      5160
gctcacatgt                                                            5170

<210> SEQ ID NO 4
<211> LENGTH: 539
<212> TYPE: DNA
<213> ORGANISM: Mus musculus

<400> SEQUENCE: 4
tggggatccc agtggggaag tcgatgttgg tgcttctcat ctctttggcc ttcgccttgt        60
gctgcatcgc tgcttacggc cccgagagga ctctgtgcgg aggggagctt gttgacacgc       120
ttcagtttgt ctgttcggac cgcggcttct acttcagcag gccttcaagc cgtgccaacc       180
gtcgcagccg tggcatcgtg gaagagtgct gcttccgcag ctgcgacctg gccctcctgg       240
agacatactg tgccaccccc gccaagtccg agagggacgt gtctacctct caggccgtac       300
ttccggacga cttccccaga taccccgtgg gcaagttctt ccaatatgac acctggagac       360
agtccgcggg acgcctgcgc agaggcctgc ctgccctcct gcgtgcccgc cggggtcgca       420
tgcttgccaa agagctcaaa gagttcagag aggccaaacg tcatcgtccc ctgatcgtgt       480
taccacccaa agaccccgcc cacggggggag cctcttcgga gatgtccagc aaccatcag       539

<210> SEQ ID NO 5
<211> LENGTH: 569
<212> TYPE: DNA
<213> ORGANISM: Mus musculus

<400> SEQUENCE: 5
```

-continued

```
tggggatccc agtggggaag tcgatgttgg tgcttctcat ctctttggcc ttcgccttgt     60
gctgcatcgc tgcttacggc cccgagaga ctctgtgcgg aggggagctt gttgacacgc    120
ttcagtttgt ctgttcggac cgcggcttct acttcagcag gccttcaagc cgtgccaacc    180
gtcgcagccg tggcatcgtg gaagagtgct gcttccgcag ctgcgacctg gccctcctgg    240
agacatactg tgccaccccc gccaagtccg agagggacgt gtctacctct caggccgtac    300
ttccggacga cttccccaga tacccccgtgg gcaagttctt ccaatatgac acctggagac    360
agtccgcggg acgcctgcgc agaggcctgc ctgccctcct gcgtgcccgc cggggtcgca    420
tgcttgccaa agagctcaaa gagttcagag aggccaaacg tcatcgtccc ctgatcgtgt    480
taccacccaa agaccccgcc cacgggggag cctcttcgga gatgtccagc aaccatcagt    540
acccatacga tgttccagat tacgtctaa                                      569

<210> SEQ ID NO 6
<211> LENGTH: 543
<212> TYPE: DNA
<213> ORGANISM: Homo sapiens

<400> SEQUENCE: 6
atgggaatcc caatggggaa gtcgatgctg gtgcttctca ccttcttggc cttcgcctcg     60
tgctgcattg ctgcttaccg ccccagtgag accctgtgcg gcggggagct ggtggacacc    120
ctccagttcg tctgtgggga ccgcggcttc tacttcagca ggcccgcaag ccgtgtgagc    180
cgtcgcagcc gtggcatcgt tgaggagtgc tgtttccgca gctgtgacct ggccctcctg    240
gagacgtact gtgctacccc cgccaagtcc gagagggacg tgtcgacccc tccgaccgtg    300
cttccggaca acttccccag ataccccgtg ggcaagttct tccaatatga cacctggaag    360
cagtccaccc agcgcctgcg caggggcctg cctgccctcc tgcgtgcccg ccggggtcac    420
gtgctcgcca aggagctcga ggcgttcagg gaggccaaac gtcaccgtcc cctgattgct    480
ctacccaccc aagaccccgc ccacgggggc gcccccccag agatggccag caatcggaag    540
tga                                                                  543

<210> SEQ ID NO 7
<211> LENGTH: 31
<212> TYPE: DNA
<213> ORGANISM: Artificial sequence
<220> FEATURE:
<223> OTHER INFORMATION: Sense primer

<400> SEQUENCE: 7
ggcgaattcc ctggctatgg ggatcccagt g                                    31

<210> SEQ ID NO 8
<211> LENGTH: 54
<212> TYPE: DNA
<213> ORGANISM: Artificial sequence
<220> FEATURE:
<223> OTHER INFORMATION: Anti-sense-HA primer

<400> SEQUENCE: 8
acgtagatct ttagacgtaa tctggaacat cgtatgggta ctgatggttg ctgg           54

<210> SEQ ID NO 9
<211> LENGTH: 26
<212> TYPE: DNA
<213> ORGANISM: Artificial sequence
<220> FEATURE:
```

<223> OTHER INFORMATION: Anti-sense primer

<400> SEQUENCE: 9
ggcagatctt cactgatggt tgctgg                                          26

<210> SEQ ID NO 10
<211> LENGTH: 20
<212> TYPE: DNA
<213> ORGANISM: Artificial sequence
<220> FEATURE:
<223> OTHER INFORMATION: Igf2 sense primer

<400> SEQUENCE: 10
gtcgcatgct tgccaaagag                                                 20

<210> SEQ ID NO 11
<211> LENGTH: 20
<212> TYPE: DNA
<213> ORGANISM: Artificial sequence
<220> FEATURE:
<223> OTHER INFORMATION: Igf2 antisense primer

<400> SEQUENCE: 11
ggtggtaaca cgatcagggg                                                 20

<210> SEQ ID NO 12
<211> LENGTH: 20
<212> TYPE: DNA
<213> ORGANISM: Artificial sequence
<220> FEATURE:
<223> OTHER INFORMATION: Igf2-HA sense primer

<400> SEQUENCE: 12
gtcgcatgct tgccaaagag                                                 20

<210> SEQ ID NO 13
<211> LENGTH: 21
<212> TYPE: DNA
<213> ORGANISM: Artificial sequence
<220> FEATURE:
<223> OTHER INFORMATION: Igf2-HA antisense primer

<400> SEQUENCE: 13
tagacgtaat ctggaacatc g                                               21

<210> SEQ ID NO 14
<211> LENGTH: 19
<212> TYPE: DNA
<213> ORGANISM: Artificial sequence
<220> FEATURE:
<223> OTHER INFORMATION: Actin sense primer

<400> SEQUENCE: 14
taccaccatg tacccagca                                                  19

<210> SEQ ID NO 15
<211> LENGTH: 24
<212> TYPE: DNA
<213> ORGANISM: Artificial sequence
<220> FEATURE:
<223> OTHER INFORMATION: Actin antisense primer

<400> SEQUENCE: 15
ctcaggagga gcaatgatct tgat                                            24